United States Patent
Glenn et al.

(10) Patent No.: US 10,363,470 B2
(45) Date of Patent: Jul. 30, 2019

(54) GOLF CLUBS AND GOLF CLUB HEADS HAVING A PLURALITY OF SENSORS FOR DETECTING ONE OR MORE SWING PARAMETERS

(71) Applicant: NIKE, Inc., Beaverton, OR (US)

(72) Inventors: Bradley C. Glenn, Columbus, OH (US); Douglas A. Thornton, Columbus, OH (US); Jeffrey A. Hadden, Delaware, OH (US)

(73) Assignee: NIKE Inc., Beaverton, OR (US)

( * ) Notice: Subject to any disclaimer, the term of this patent is extended or adjusted under 35 U.S.C. 154(b) by 392 days.

(21) Appl. No.: 14/951,930

(22) Filed: Nov. 25, 2015

(65) Prior Publication Data

US 2017/0144022 A1    May 25, 2017

(51) Int. Cl.
| | |
|---|---|
| *G06K 9/00* | (2006.01) |
| *G06T 7/20* | (2017.01) |
| *A63B 53/04* | (2015.01) |
| *A63B 60/46* | (2015.01) |

(52) U.S. Cl.
CPC .............. *A63B 60/46* (2015.10); *A63B 53/04* (2013.01); *G06K 9/00342* (2013.01); *G06T 7/20* (2013.01)

(58) Field of Classification Search
CPC ...... A63B 24/0006; A63B 53/04; A63B 60/46
See application file for complete search history.

(56) References Cited

U.S. PATENT DOCUMENTS

| | | | |
|---|---|---|---|
| 2011/0053698 A1* | 3/2011 | Stites | A63B 69/36 473/223 |
| 2011/0305369 A1* | 12/2011 | Bentley | G06K 9/00342 382/103 |
| 2013/0203518 A1* | 8/2013 | Hatton | A63B 53/047 473/223 |
| 2014/0200092 A1* | 7/2014 | Parke | G01P 15/0888 473/223 |
| 2016/0158598 A1* | 6/2016 | Dolezel | A63B 53/04 473/223 |
| 2016/0166902 A1 | 6/2016 | Day et al. | |
| 2016/0303443 A1 | 10/2016 | Boggs et al. | |
| 2016/0310820 A1* | 10/2016 | Kline | A63B 71/0619 |

* cited by examiner

*Primary Examiner* — Changhyun Yi
(74) *Attorney, Agent, or Firm* — Banner & Witcoff, Ltd.

(57) ABSTRACT

A golf club head having accelerometer and gyroscope sensors measuring swing motion acceleration and angular rate values. Inputs of force and torque to the golf club head during the swing motion may be unknown, such that a system of motion equations may be used to calculate functions for the unknown input force and torque, as well as roll angle and pitch angle for the golf club head, and compensate for gyroscope bias, without using static leveling processes.

23 Claims, 12 Drawing Sheets

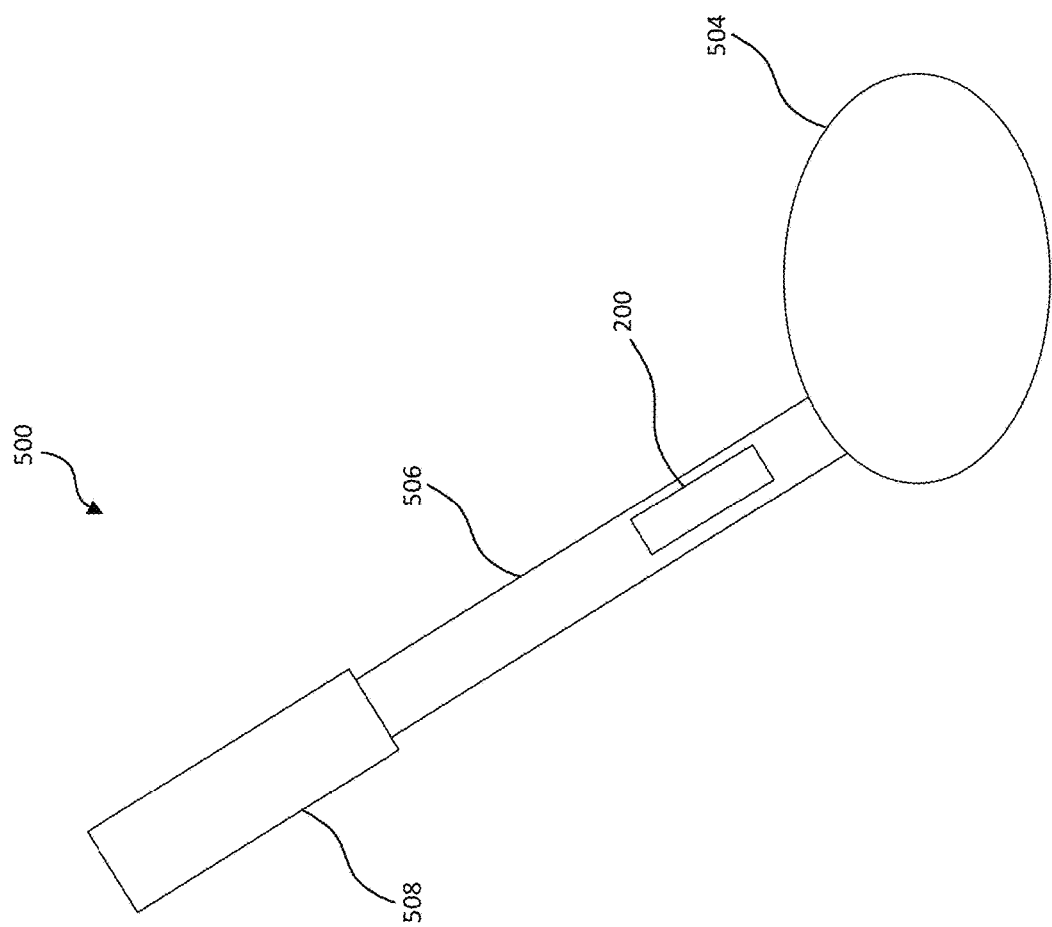

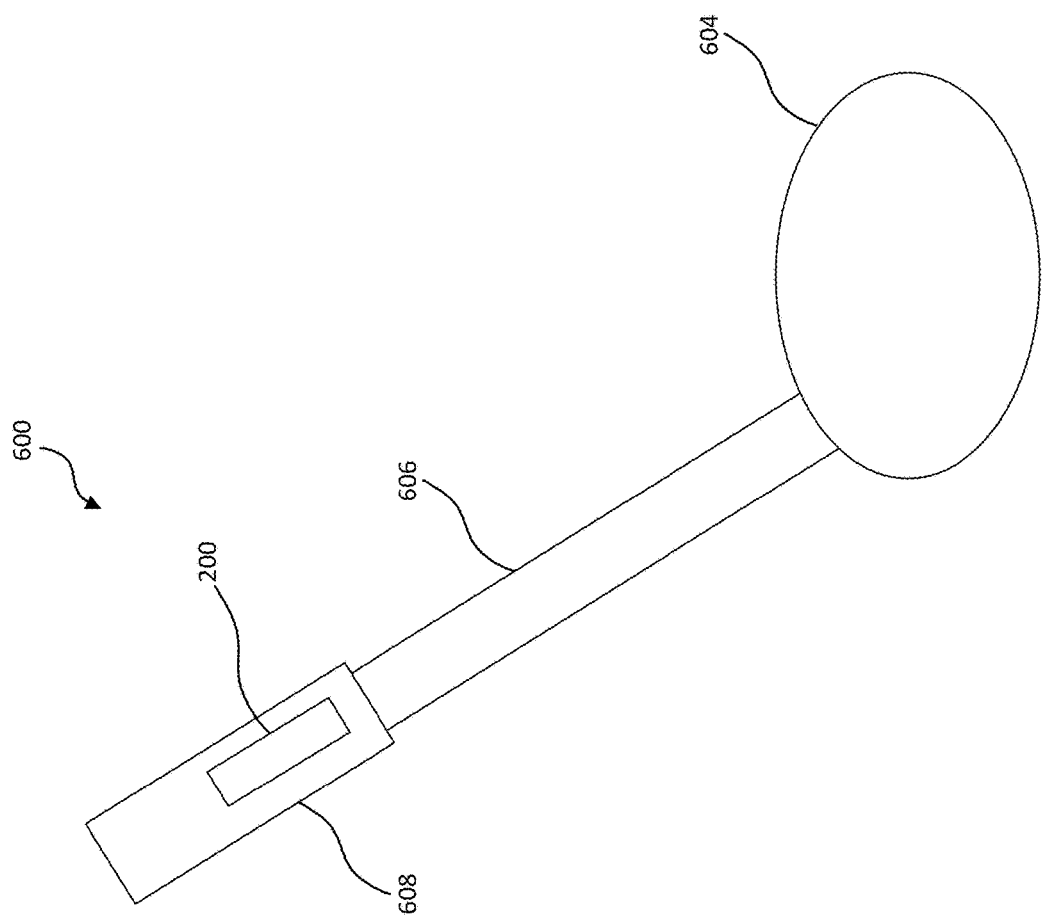

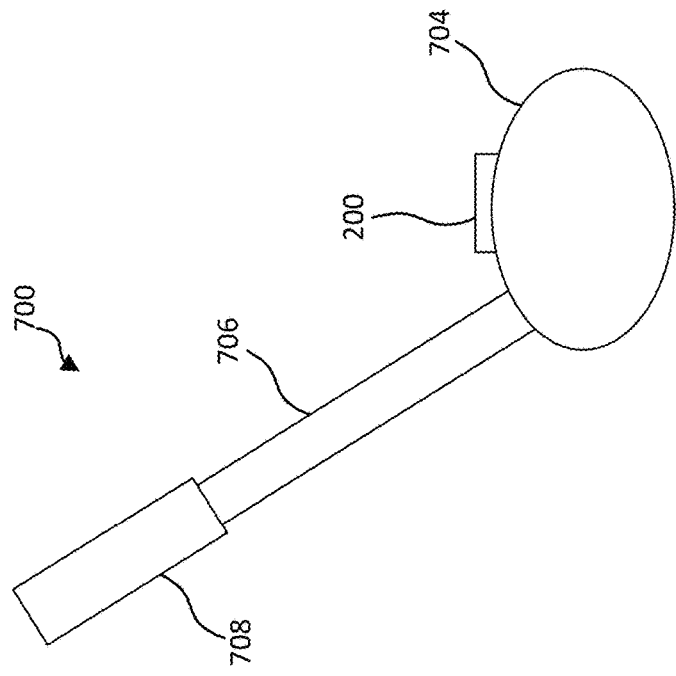
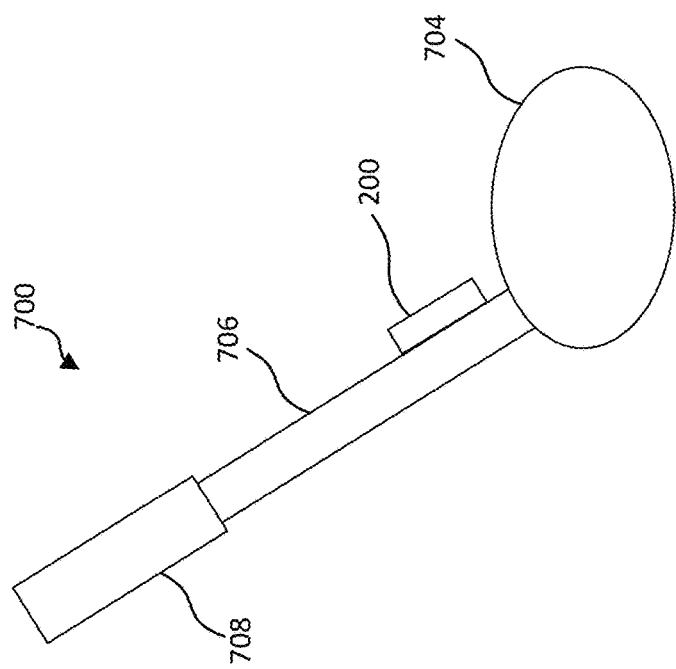

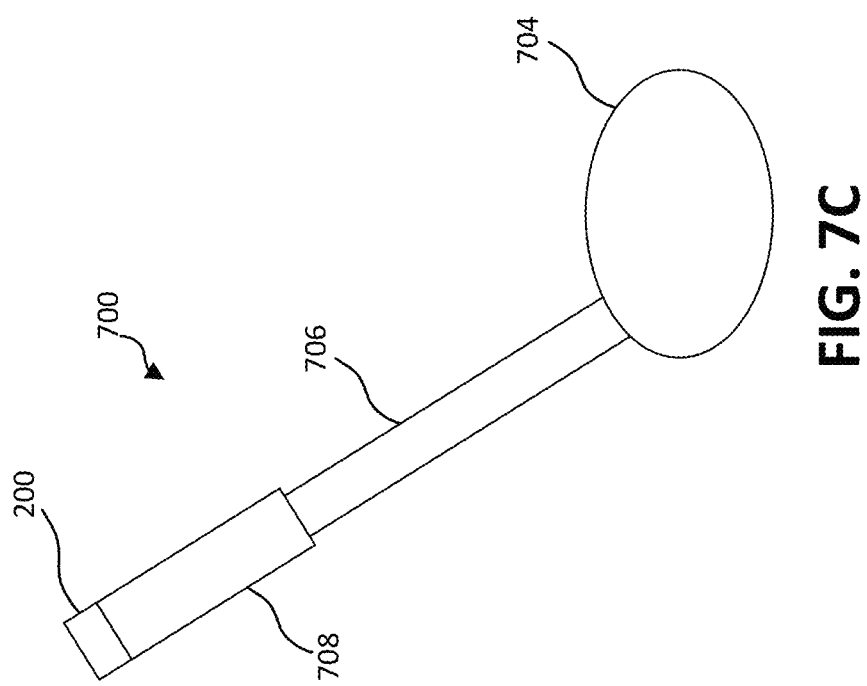

GOLF CLUBS AND GOLF CLUB HEADS HAVING A PLURALITY OF SENSORS FOR DETECTING ONE OR MORE SWING PARAMETERS

TECHNICAL FIELD

Aspects of this disclosure generally relate to golf clubs and golf club heads. More particularly, aspects of this disclosure relate to golf clubs and golf club heads having a plurality of sensors for detecting one or more swing parameters.

BACKGROUND

Golf is enjoyed by a wide variety of players—players of different genders and dramatically different ages and/or skill levels. Golf is somewhat unique in the sporting world in that such diverse collections of players can play together in golf events, even in direct competition with one another (e.g., using handicapped scoring, different tee boxes, in team formats, etc.), and still enjoy the golf outing or competition. These factors, together with the increased availability of golf programming on television (e.g., golf tournaments, golf news, golf history, and/or other golf programming) and the rise of well-known golf superstars, at least in part, have increased golf's popularity in recent years, both in the United States and across the world.

Golfers at all skill levels seek to improve their performance, lower their golf scores, and reach that next performance "level." Manufacturers of all types of golf equipment have responded to these demands, and in recent years, the industry has witnessed dramatic changes and improvements in golf equipment. For example, a wide range of different golf ball and club models now are available, with balls designed to complement specific swing speeds and/or other player characteristics or preferences, e.g., with some balls designed to fly farther and/or straighter; some designed to provide higher or flatter trajectories; some designed to provide more spin, control, and/or feel (particularly around the greens); some designed for faster or slower swing speeds; etc. Additionally, the market has seen dramatic changes and improvements in putter designs, golf club head designs, shafts, and grips in recent years. Further, other technological advancements have been made in an effort to better match the various elements and/or characteristics of the golf club and characteristics of a golf ball to a particular user's swing features or characteristics In addition to the golf equipment, the mechanics of the golf swing itself are also of interest to the player eager to improve his/her performance. Qualitative evaluation of a user's swing by a trained golfing professional has traditionally been helpful in correcting certain errors and honing skills of players of all experience levels, but advancement in a technology for providing quantitative analysis of a user's golf swing would be welcome in the art.

BRIEF SUMMARY

In light of the foregoing background, the following presents a simplified summary of the present disclosure in order to provide a basic understanding of some aspects of the various implementations of this disclosure. This summary is not an extensive overview of the embodiments described herein. It is not intended to identify key or critical elements, or to delineate the scope of the embodiments described in this disclosure. The following summary merely presents some concepts of the embodiments of this disclosure in a simplified form as a prelude to the more detailed description provided below.

In one aspect, this disclosure may relate to non-transitory, computer-readable media that have computer-executable instructions that, when executed, may cause a computer device to receive sensor data from an inertial measurement unit that is attached to an object moving between a first time instant and a second time instant. Acceleration and angular rate measurements may be extracted from the received sensor data. A system of motion equations for the moving object may be constructed using an unknown input observer that compensates for gyroscope bias. An estimated output error may be calculated from the received sensor data. The estimated output error may be used in the system of motion equations. Further, the system of motion equations may be solved, and functions of input force, input torque, roll angle, and pitch angle may be outputted from the solutions to the system of motion equations. Additionally, the position of the moving object may be calculated using the output functions.

In another aspect, this disclosure may include a golf club head that has an accelerometer sensor, a gyroscope sensor, a processor, and a non-transitory computer-readable medium that stores computer-readable instructions that may be executed by a processor. When executed, the computer-readable instructions may cause the processor to receive sensor data from the accelerometer and the gyroscope as a result of a motion of the golf club head. Further, the computer-readable instructions may extract acceleration and angular rate measurements from the sensor data. A system of motion equations may be constructed using an unknown input observer that compensates for gyroscope bias. Further, an estimated output error may be calculated from the received sensor data. The estimated output error may be used in the system of motion equations for the golf club. The computer-readable instructions may further solve the system of motion equations, and output functions describing a position of the golf club head during the motion.

In yet another aspect, this disclosure relates to a method that may receive, by a computing device, sensor data from an inertial measurement unit attached to a moving object. The method may construct a system of motion equations that compensates for gyroscope bias, and calculate an estimated output error using the received sensor data. The estimated output error may be utilized in the system of motion equations, and the motion equations may be solved to output functions describing a position of the moving object.

Aspects of this disclosure address one or more of the issues mentioned above by disclosing methods, systems, non-transitory computer readable media, and apparatuses for calculating a position of a golf club throughout a swing motion using sensor data received from an inertial measurement unit, and without knowing an input force and an input torque to the golf club. Aspects of the disclosure may also be provided in a non-transitory computer-readable medium having computer-executable instructions to perform one or more of the process steps described herein.

This Summary is provided to introduce a selection of concepts in a simplified form that are further described below in the Detailed Description. The Summary is not intended to identify key features or essential features of the claimed subject matter, nor is it intended to be used to limit the scope of the claimed subject matter.

BRIEF DESCRIPTION OF THE DRAWINGS

The present invention is illustrated by way of example and is not limited in the accompanying figures in which like reference numerals indicate similar elements.

FIG. 5 schematically depicts another implementation of an instrumented golf club, according to one or more aspects described herein.

FIG. 6 schematically depicts yet another implementation of an instrumented golf club, according to one or more aspects described herein.

FIGS. 7A-7C schematically depict implementations of instrumented golf clubs, according to one or more aspects described herein.

DETAILED DESCRIPTION

Golf swing analysis may be used as a training aid for golfers of all ability levels. In one example, numerical analysis, and optionally, computer visualization, of a golf swing may be utilized to identify inefficiencies, or errors, in a user's golf swing motion.

Figure 1:
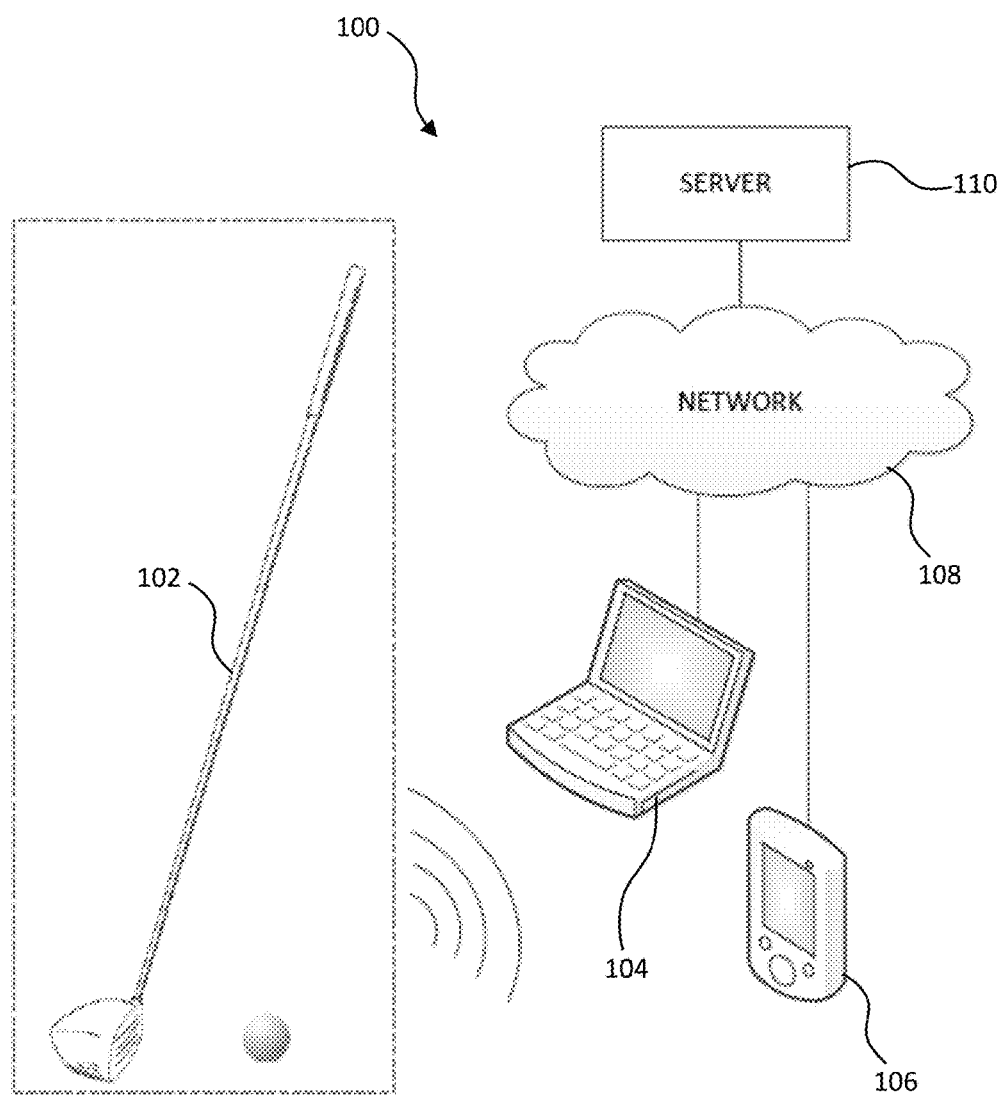
FIG. 1 illustrates an example golf analysis system according to one or more aspects described herein.

FIG. 1 illustrates an example system and environment 100 in which various aspects described herein may be used and implemented. Sensor data from one or more sensors may be processed to assess one or more characteristics of a user's golf swing. As such, a golf club 102 may be outfitted with integrated sensors and/or sensors that are removably-coupled to the golf club 102. As such, the golf club 102 may be referred to as an instrumented golf club. These sensors may include one or more accelerometers configured to detect linear accelerations along one or more axes, and/or one or more gyroscopes, configured to detect angular velocities about one or more axes. In one example, golf club 102 may be configured with three accelerometers aligned along three orthogonal (mutually-perpendicular) axes as well as three gyroscopes sensitive to angular velocities about each of the three orthogonal axes. These three accelerometers and three gyroscopes may be integrated into an inertial measurement unit (IMU), which will be discussed in further detail below. Data from these sensors may be processed on-board the golf club 102 such that raw sensor data may be transformed into data describing of one or more motions of a golf club through a swing. Subsequently, this processed data may be communicated to a remote computing device for review and/or further processing. Alternatively, data from the sensors may be communicated as raw sensor data to be processed by a remote computing device, such as devices 104 and/or 106. Accordingly, the golf club 102 may comprise a transceiver configured to allow for wired and/or wireless communication of data between the one or more sensors, and the devices 104 and/or 106. In one example, devices 104 and 106 may comprise consumer electronic equipment, such that device 104 may be a personal computer 104 and device 106 may be a mobile communication device, such as a tablet computer, a personal data assistant (PDA), a smartphone, and/or combinations thereof. Further, personal computer 104 may include one or more laptop computers or desktop computers. Devices 104 and 106 may be connected, via network 108, to a variety of other devices and destinations, including server 110. As such, devices 104 and 106 may include network interfaces that are either wired or wireless or may have both wired and wireless connection interfaces. Wireless connections may be short range or long range, and may include Wi-Fi, BLUETOOTH, infrared, satellite communications, cellular communications and the like. Some devices (e.g., device 106) may include multiple network interfaces and have the capability of transmitting and receiving information over different interfaces depending on a destination/source, time of day, type of information being sent/received and the like. In one example, server 110 may be configured to collect data from various user devices as well as to distribute information such as fitness challenges, golf recommendations, product offers and the like.

As discussed above, a golf club, such as golf club 102, may comprise an inertial measurement unit (IMU) employed to generate data corresponding to the motion of a golf club throughout a golf swing motion between a first time instant and a second time instant. In one example, the first time instant may correspond to a start of a golf swing motion, or may correspond to a predetermined instant prior to, or after, a detected start of a golf swing motion. Further, the second time instant may correspond to an end of a golf swing motion, or may correspond to a predetermined instant after, or before, a detected end of a golf swing motion, among others. As such, these predetermined times may include any time values, without departing from the scope of these disclosures. In turn, this IMU data may be processed to determine information about the motion of the golf club 102 throughout a swing.

Figure 2:
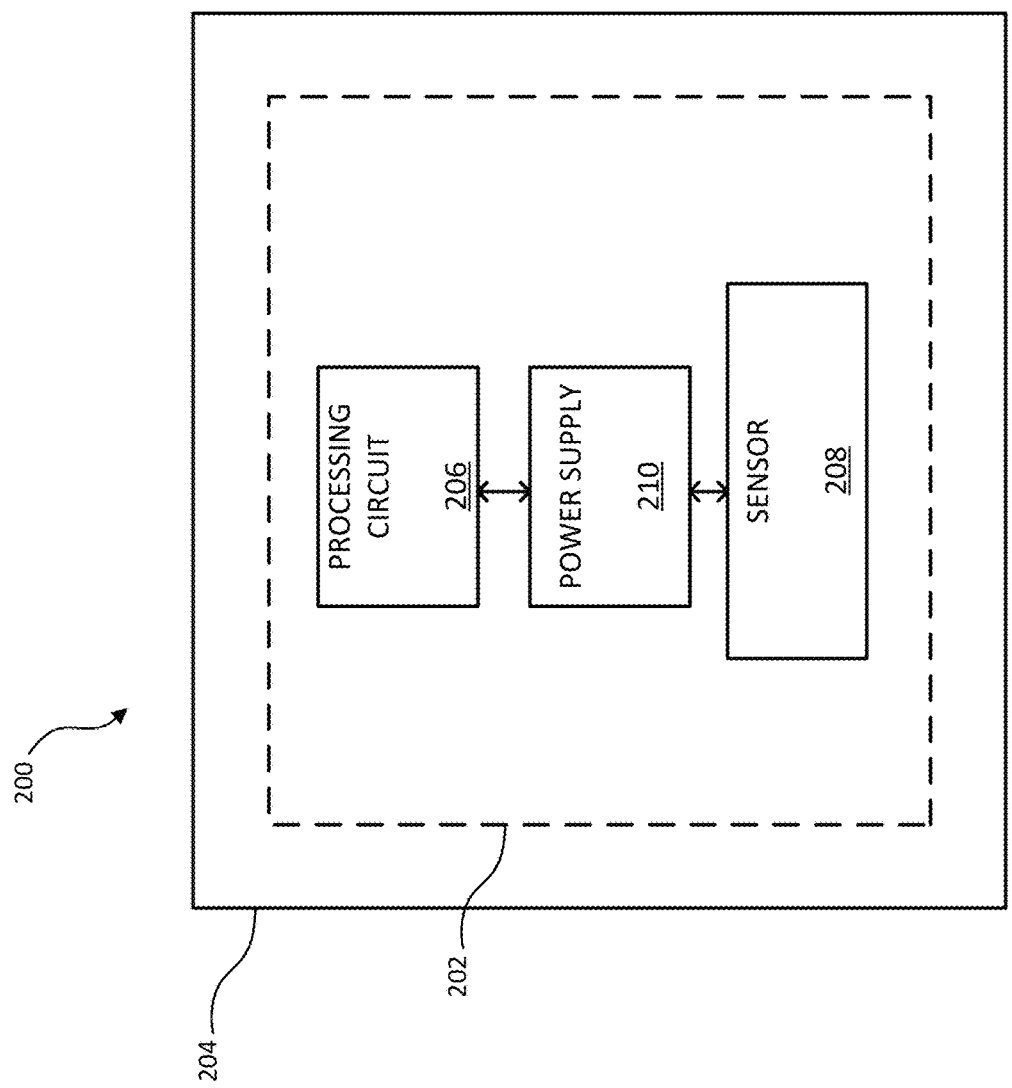
FIG. 2 depicts an illustrative inertial measurement unit, according to one or more aspects described herein.

FIG. 2 illustrates one example of an inertial measurement unit (IMU) 200 that may be employed, according to various examples described in this disclosure, to measure one or more characteristics of a golf swing. In one implementation, the IMU 200 may comprise an IMU integrated circuit 202 having a protective outer casing structure 204 that is configured to enclose and protect the integrated circuit 202 from exposure to an external environment. As such, the casing structure 204 may comprise any shape, size and/or material configured to protect an integrated circuit, such as IMU integrated circuit 202. In one specific example, the casing structure 204 may comprise a material (e.g. a polymer) configured to allow transmission of radio waves, and such that wireless communication between the IMU integrated circuit 202, and an external computing device, such as device 104 and/or device 106, may be facilitated. In other examples, wired communication between the IMU integrated circuit 202 and another computing device, such as devices 104 and 106, may be facilitated. The IMU integrated circuit 202 may include a processing circuit 206. Processing circuit 206 may be utilized to process data received from sensor 208. Accordingly, processing circuit 206 is described in further detail in relation to FIG. 3.

The IMU integrated circuit 202 may also include a power supply 210, for providing power to the sensor 208, and the processing circuit 206. The power supply 210 may comprise, for example, a battery.

As discussed above, the IMU integrated circuit 202 may be configured to generate sensor data responsive to a golf swing. As such, sensor 208 may represent a microelectromechanical systems (MEMS) chip/circuit containing three accelerometers sensitive to linear accelerations along three orthogonal axes, and three gyroscopes sensitive to angular velocities about the three orthogonal axes. Additionally or alternatively, the sensor 208 may include a magnetometer, a strain gauge, or an impact sensor. As discussed in further detail below, output data from one or more of these three accelerometers and/or three gyroscopes may be processed, such as by processing circuit 206, in order to calculate and describe a motion of a golf club during a swing. While the description that follows includes more details of data processing from, for example, sensor 208, example processes may calculate, among others, a velocity of the golf club 102 (or club head) during a golf swing, an acceleration of the club (or club head) during a golf swing, an angle of the golf club (or club head) during a golf swing (e.g., relative to one or more reference points), a swing tempo, an impact of the ball with the golf club head during a golf swing, aspects of the impact of the ball with the golf club head during a golf swing (e.g., loft angle, lie angle, and/or face angle, etc.), etc. In additional or alternative implementations, sensors may be configured to measure the position (e.g. a spatial position with regard to a particular frame of reference) of the golf club 102 at various points in time. In this way, acceleration, velocity, positioning of a golf club 102 may be determined and analyzed in three dimensions. Further, data from sensor 208 may be utilized to create a graphical representation (e.g., a picture or video) of a golf swing. For example, a swing path may be graphically represented in 3 dimensions along an X-Y-Z frame of reference.

In one example, the IMU integrated circuit 202 may be implemented on a single physical chip, and housed within the casing structure 204. Accordingly, the casing structure 204, containing the IMU integrated circuit 202 may be integrated into, or coupled to, a golf club, such as golf club 102. In another example, one or more of the processing circuit 206, the power supply 210, and/or the sensor 208 of the IMU integrated circuit 202 may be implemented on one or more separate physical hardware elements. These separate physical hardware elements may all be integrated into/coupled to a golf club, such as golf club 102. Alternatively, one or more of these separate physical hardware elements may be integrated into/coupled to golf club 102, while one or more of the separate physical hardware elements may be positioned remote to golf club 102, linked by a wired or wireless network connection.

Figure 3:
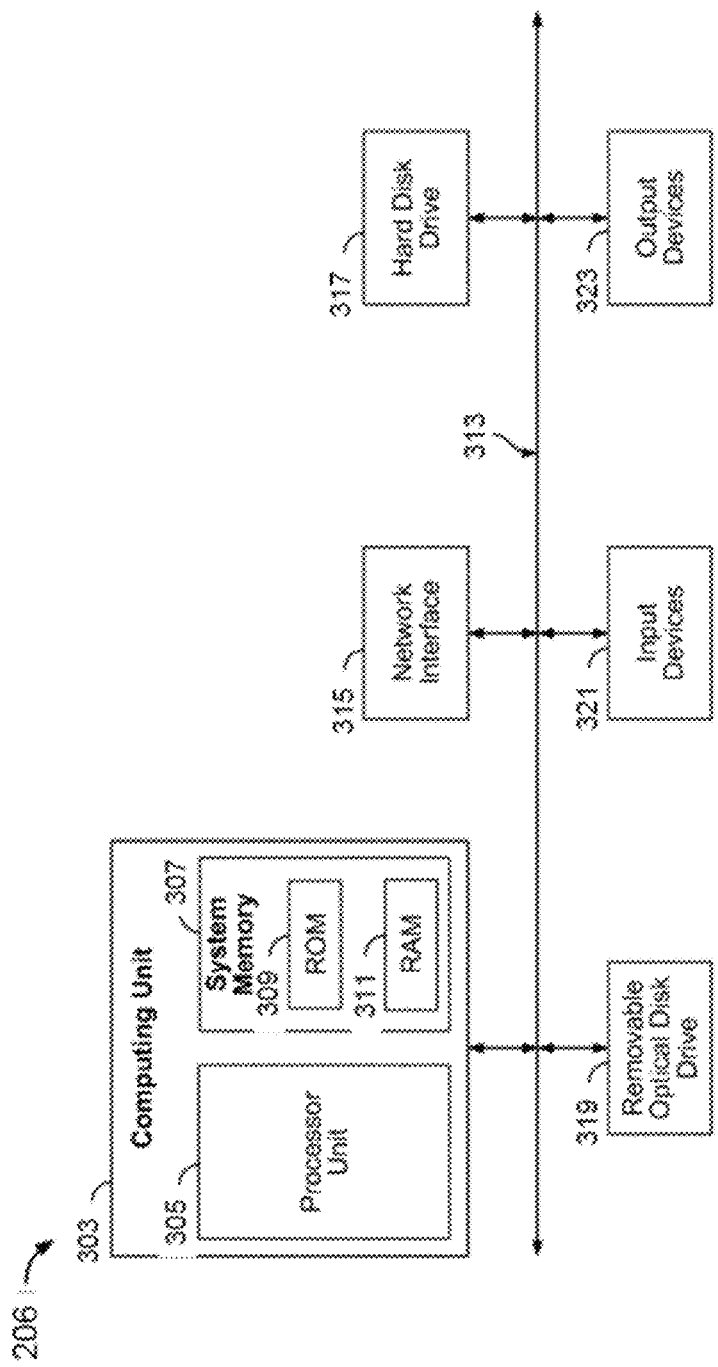
FIG. 3 depicts an illustrative processing circuit, according to one or more aspects described herein.

FIG. 3 shows one illustrative example of the processing circuit 206 that may be used to implement various aspects and features described herein. In one example, processing circuit 206 may be utilized as part of the IMU integrated circuit 202. As such, the processing circuit 206 may be configured to perform any desired operation on one or more data streams received from sensor 208. Further, it will be appreciated that the processing circuit 206 may execute multiple calculations, in parallel or serial, at a very high throughput frequency using the received sensor data, in order to analyze a golf swing. As such, processing circuit 206 may be configured to execute hundreds of thousands, millions, or billions or more calculations per second using sensor data received from sensor 208. In one example, processing circuit 206 may be configured to execute one or more integration processes on large, coupled systems of differential equations. In other examples, processor 206 may execute curve smoothing, noise filtering, outlier removal, amplification, and summation processes, and the like. In some examples, the IMU indicated circuit 202 may not utilize the processing circuit 206 to process sensor data received from the sensor 208. Instead, the raw sensor data may be communicated to one or more remote computing devices, such as devices 104 and 106, among others. Further details of the analysis of received sensor data from sensor 208 are described below.

Processing circuit 206 may act as device 104, device 106, or server 110. As seen in FIG. 3, the processing circuit 206 may include a computing unit 303. The computing unit 303 typically includes a processing unit 305 and a system memory 207. The processing unit 305 may be any type of processing device for executing software instructions, but will conventionally be a microprocessor device. The system memory 307 may include both a read-only memory (ROM) 309 and a random access memory (RAM) 311. As will be appreciated by those of ordinary skill in the art, both the read-only memory (ROM) 309 and the random access memory (RAM) 311 may store software instructions for execution by the processing unit 305.

The processing unit 305 and the system memory 307 are connected, either directly or indirectly, through a bus 313 or alternate communication structure to one or more peripheral devices. For example, the processing unit 305 or the system memory 307 may be directly or indirectly connected to additional memory storage, such as the hard disk drive 317, the removable optical disk drive 319. Additional buses may be included as needed or desired. Processing circuit 306 may further use or interface with other memory storage mediums such as solid state drives, removable magnetic disk drives and flash memory cards. The processing unit 305 and the system memory 307 also may be directly or indirectly connected to one or more input devices 321 and one or more output devices 323. The input devices 321 may include, for example, a keyboard, touch screen, a remote control pad, a pointing device (such as a mouse, touchpad, stylus, trackball, or joystick), a scanner, a camera or a microphone. The output devices 323 may include, for example, a monitor display, television, printer, stereo, or speakers.

Still further, the computing unit 303 may be directly or indirectly connected to one or more network interfaces 315 for communicating with a network 108. This type of network interface 315, also sometimes referred to as a network adapter or network interface card (NIC), translates data and control signals from the computing unit 303 into network messages according to one or more communication protocols, such as the Transmission Control Protocol (TCP), the Internet Protocol (IP), and the User Datagram Protocol (UDP). Network adapters may be wireless or wired or combinations thereof. These protocols are well known in the art, and thus will not be discussed here in more detail. An interface 315 may employ any suitable connection agent for connecting to a network, including, for example, a wireless transceiver, a power line adapter, a modem, or an Ethernet connection. Connection agents may similarly be wireless or wired or a combination thereof. Accordingly, using interface 315, processing circuit 206 may be able to access wide area networks such as the Internet in addition to local area networks. Golf swing data may be transmitted to, or received from, local or remote network sources (not shown). As such, the processor unit 305 may be configured to provide processed data signals to network interface 315 (which may be a transceiver or transmitter). Accordingly, transceiver 305 may be configured to transmit the processed data signals to a remote computing system, such as device 104 or device 106. In one example, the processed data may be transmitted wirelessly. In another example, wired transmission of a processed data from the IMU processing circuit 206 may be utilized.

The processing circuit 206 may be connected to or otherwise include one or more other peripheral devices, such as a telephone. The telephone may be, for example, a wireless smartphone. As known in the art, this type of telephone communicates through a wireless network using radio frequency transmissions. In addition to simple communication functionality, a smartphone may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files, and the like. Because of the data management capability of this type of telephone, a user may connect the telephone with the processing circuit 206 so that their data maintained may be synchronized.

Still other peripheral devices may be included with or otherwise connected to a processing circuit 206 of the type illustrated in FIG. 3, as is well known in the art. In some cases, a peripheral device may be permanently or semi-permanently connected to the computing unit 303. For example, with many computers, the computing unit 303, the hard disk drive 317, the removable optical disk drive 319 and a display may be semi-permanently encased in a single housing. Still other peripheral devices may be removably connected to the processing circuit 206. The processing circuit 206 may include, for example, one or more communication ports through which a peripheral device can be connected to the computing unit 303 (either directly or indirectly through the bus 313). These communication ports may thus include a parallel bus port or a serial bus port, such as a serial bus port using the Universal Serial Bus (USB) standard (or variations thereof) or the IEEE 1394 High Speed Serial Bus standard (e.g., a Firewire port), or other similar communication means known and used in the art. Additionally or alternatively, the processing circuit 206 may include a wireless data port, such as a Bluetooth interface, a Wi-Fi interface, an infrared data port, or the like.

It should be appreciated that a computing device employed according various examples described herein may include more elements than the processing circuit 206 illustrated in FIG. 3, fewer elements than the processing circuit 206, or a different combination of elements than the processing circuit 206.

Some implementations described herein, for example, may employ one or more computing devices that are intended to have a very specific functionality, such as a server computer. These computing devices may thus omit unnecessary peripherals, such as the network interface 315, removable optical disk drive 319, printers, scanners, external hard drives, and the like. Some implementations described herein may alternately or additionally employ computing devices that are intended to be capable of a wide variety of functions, such as a desktop or laptop personal computer. These computing devices may have any combination of peripheral devices or additional components as desired.

As previously described, the IMU integrated circuit 202 may be configured to generate sensor data responsive to a motion of a golf club between a first time instant and a second time instant. Accordingly, the IMU 200, of which the IMU integrated circuit 202 is a constituent, may be integrated into, or coupled to (in one example, removably-coupled to) a golf club, such as golf club 102. In this regard, FIGS. 4, 5, 6, 7A-7C schematically-depict different configurations of golf club incorporating the IMU 200.

Figure 4:
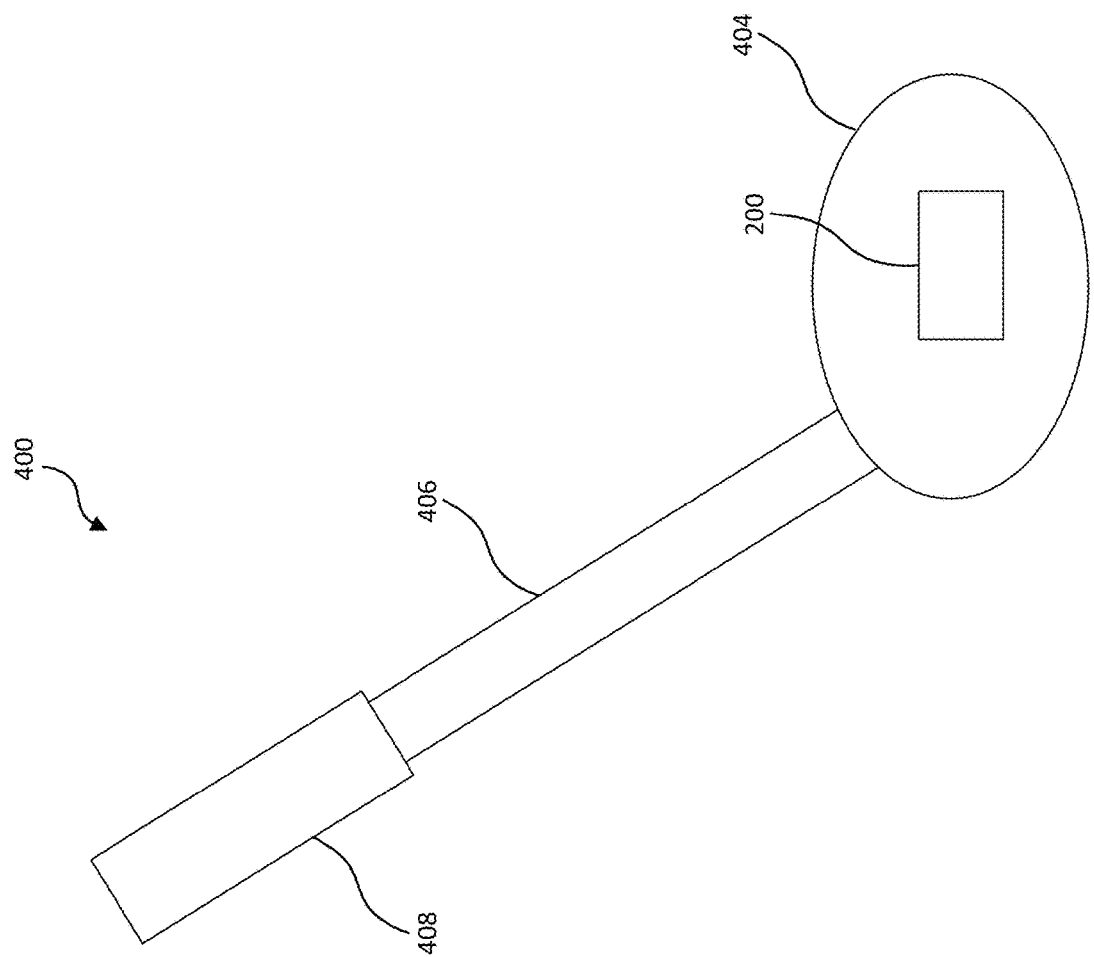
FIG. 4 schematically depicts an instrumented golf club, according to one or more aspects described herein.

FIG. 4 schematically depicts a golf club 400, which may be similar to golf club 102, including a club head 404, a shaft 406, and a grip portion 408. The club head 404 may correspond to any golf club head type, including any iron-type club head, any driver-type club head, any fairway wood-type club head, any hybrid or recovery wood-type club head, or any putter-type, among others. The club head 404 may be embodied with any geometrical features or volumes without departing from the scope of these disclosures. Further, the shaft 406 and grip 408 may include any golf club shaft and grip types, without departing from the scope of these disclosures. In one example, the golf club 400 may incorporate IMU 200 into the club head 404. As such, multiple options for removable or permanent coupling of the IMU 200 within the club head 404 will be recognized, and may be utilized without departing from the scope of the disclosures herein.

Regardless of the type and quantity of sensors within the club head 404, embodiments of the present disclosure may be constructed so as to not interfere with the aerodynamics of the club 400. Moreover, club head 404 may be configured so that the masses and arrangement of the included components do not change the balance or center of gravity of the club head 404. In one implementation, the mass of the club head 404 is less than 6% from the mass of an unmodified club head. In certain implementations, the moment of inertia ("MOI") is also not significantly altered. In one implementation, the MOI will be about 1500 g·cm$^2$ with a standard deviation of 200 g·cm$^2$. However, other values for MOI, and standard deviation thereof, may be utilized with golf club head 404, without departing from these disclosures.

FIG. 5 schematically depicts another implementation of an instrumented golf club 500, which may be similar to golf club 400 and golf club 102, and include a golf club head 504 similar to golf club head 404, a shaft 506 similar to shaft 406, and a grip 508 similar to grip 408. However, in contrast to golf club 400, golf club 500 may incorporate the IMU 200 into the shaft 506. As such, the IMU 200 may be coupled within shaft 506 such that it is user-removable, or the IMU 200 may be non-user-removable from the shaft 506. Further, various implementations of shaft 506, configured to receive the IMU 200, may be utilized without departing from the scope of these disclosures. FIG. 6 schematically depicts another implementation of an instrumented golf club 600, which may be similar to golf club 400 and golf club 102, and include a golf club head 604 similar to golf club head 404, a shaft 606 similar to shaft 406, and a grip 608 similar to grip 408. However, in contrast to golf club 400, golf club 600 may incorporate the IMU 200 into the grip 608. As such, the IMU 200 may be coupled within or beneath grip 608 such that it is user-removable, or the IMU 200 may be incorporated into the club 600 during manufacturing such that the IMU 200 may be non-user-removable from the grip 608. Further, various implementations of grip 608, configured to receive the IMU 200, may be utilized without departing from the scope of these disclosures.

In other examples, a sensor device, such as IMU 200, may be externally-coupled to a golf club, such that the structure of the golf club does not have to be altered to internally house the IMU 200. As such, the IMU 200 may be removably-coupled to a golf club 700, as schematically depicted in FIG. 7A. Accordingly, golf club 700 may be similar to golf club 400 and golf club 102, including a golf club head 704 similar to golf club head 404, a shaft 706 similar to shaft 406, and a grip 708 similar to grip 408. In particular, FIG.

7A schematically depicts the IMU 200 externally affixed to shaft 706. As such, any coupling mechanism may be utilized to removably or permanently couple the IMU 200 to the shaft 706, without departing from the scope of these disclosures. In other examples, the IMU 200 may be externally-coupled to the club head 704, as schematically depicted in FIG. 7B, or externally-coupled to the grip 708, as schematically depicted in FIG. 7C.

Figure 8:
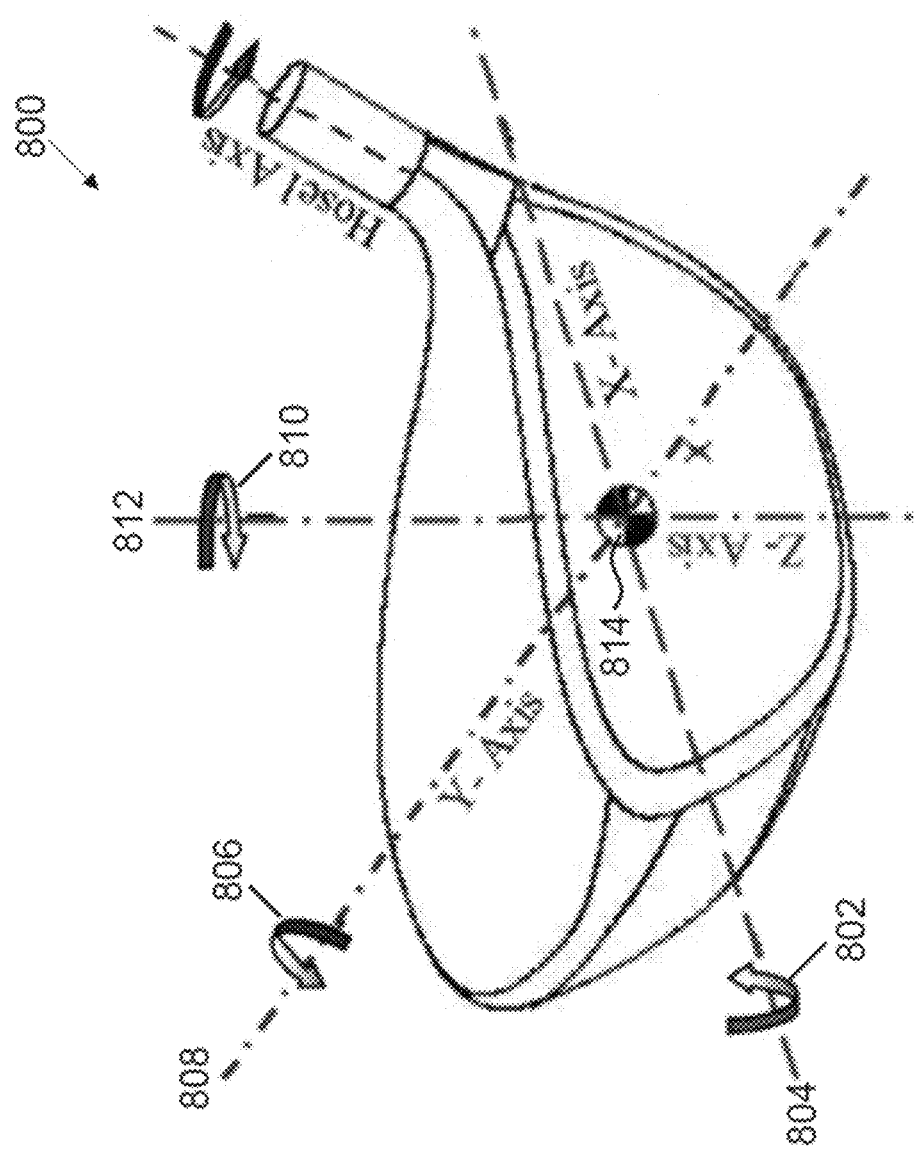
FIG. 8 schematically depicts a golf club head with orthogonal axes along and about which sensors may measure linear accelerations and angular velocities, according to one or more aspects described herein.

As previously described, one or more implementations described herein may utilize a sensor, such as sensor 208, having three accelerometers sensitive to linear accelerations along three orthogonal axes, and three gyroscopes sensitive to angular velocities about the three orthogonal axes. As such, the three accelerometers and three gyroscopes may be referenced relative to Cartesian axes; x-axis, y-axis, and z-axis. FIG. 8 schematically depicts a golf club head 800 with one implementation of Cartesian axes along and about which the three accelerometers and three gyroscopes may be sensitive to linear accelerations and angular velocities, respectively. As illustrated in FIG. 8, Cartesian axes may be defined with an x-axis 804 parallel with a striking face of the golf club head 800, a y-axis 808 normal to the x-axis 804, and a z-axis 812 normal to the x-axis 804 and the y-axis 808. Other definitions and/or orientations of the Cartesian axes may be utilized without departing from this disclosure. As such, in one example, a first gyroscope may be configured to measure an angular velocity (i.e., see arrow 802) about the x-axis 804 and a first accelerometer may be configured to measure a linear acceleration along the x-axis 804. A second gyroscope may be configured to measure an angular velocity (i.e., see arrow 806) about the y-axis 808, and a second accelerometer may be configured to measure a linear acceleration along the y-axis 808. A third gyroscope may be configured to measure an angular velocity (i.e., see arrow 810) about the z-axis 812, and a third accelerometer may be configured to measure a linear acceleration along the z-axis 812. In one implementation, the first gyroscope may be positioned at approximately position 814 (at approximately the center of the gravity of the club head 800 along the x-axis 804). In yet another implementation, the second and/or third gyroscope may also be located substantially at or approximately at position 814. In another implementation, one or more of the gyroscopes may be positioned slightly below the center of gravity.

In this description that follows, and in particular, in Equations 1-29, reference is made to an x-axis, a y-axis, and a z-axis. It should be understood that these references, in particular in Equations 1-29, are not limited to the example depicted in FIG. 8. Axes 804, 808, and 812 could be re-oriented relative to club head 800 in FIG. 8, without departing from the scope of these disclosures. As such, it should be understood that the x-axis, y-axis, and z-axis references used in Equations 1-29 in the following disclosure are used to refer to three orthogonal axes. In this way, it is not necessary for the x-axis, y-axis, and z-axis used in Equations 1-29 to align with x-axis 804, y-axis 808, and z-axis 812 schematically-depicted in FIG. 8. Those Equations 1-29 may be utilized with sensor data associated with a club head, such as club head 800, having an x-axis, y-axis, and z-axis in any orientation relative to the club head 800, as long as the axes are orthogonal to one another. Accordingly, x-axis 804, y-axis 808, and z-axis 812 in FIG. 8 merely depict one option for an orientation of the axes.

Sensor data from an IMU, such as IMU 200, may be utilized to mathematically describe motion of a golf club during a golf swing. This mathematical description may include one or more functions (e.g. functions with respect to time) that may be utilized to calculate the position of a golf club at any given instant in time between defined start and end points of a golf swing.

As such, these functions may be used to graphically plot a swing arc, among others (e.g. plot in three dimensions for display on a computer, such as one or more of devices 104 and 106). In the description that follows, a system and methodology for calculating the position of a golf club (e.g. a golf club head) based on data received from three accelerometers and three gyroscopes (e.g. using IMU 200) is described. In one example, only linear accelerations along three orthogonal axes and angular velocities about the three orthogonal axes are used to calculate functions describing the position of a golf club at all points in time during a golf swing. As such, the inputs to a golf club during a golf swing, which will include a force and a torque input from a user swinging the golf club, may be unknown.

Large forces and torques may be imparted on a golf club during a golf swing. As such, in some instances, a gyroscope sensor, such as one or more of the gyroscopes of IMU 200, may saturate at one or more instances during a golf swing motion. In other words, an actual angular velocity about one or more axes may be higher than an upper limit of a range of angular velocities that a gyroscope can measure. Additionally, a gyroscope measurement may include a bias error. Conventionally, a gyroscope bias may be compensated for using a static leveling method, which involves holding the gyroscope sensor, and thus, the object to which the sensor is attached/integrated into, completely still. However, the systems and methodology described herein, such as those described in relation to at least FIGS. 9 and 10, may be utilized to determine a position of a golf club at all instances during a golf swing, and taking into account one or more gyroscopes saturating, as well as compensating for gyroscope bias, without using static leveling. In this way, the described systems and methodology can be used, for example, for on-course analysis of a golf swing such that a user does not have to rest an instrumented golf club, such as club 102, perfectly still (static leveling) before analysis of the golf swing. Additionally, the systems and methodology described do not require knowledge of one or more input forces or torques to the golf club head.

Figure 9:
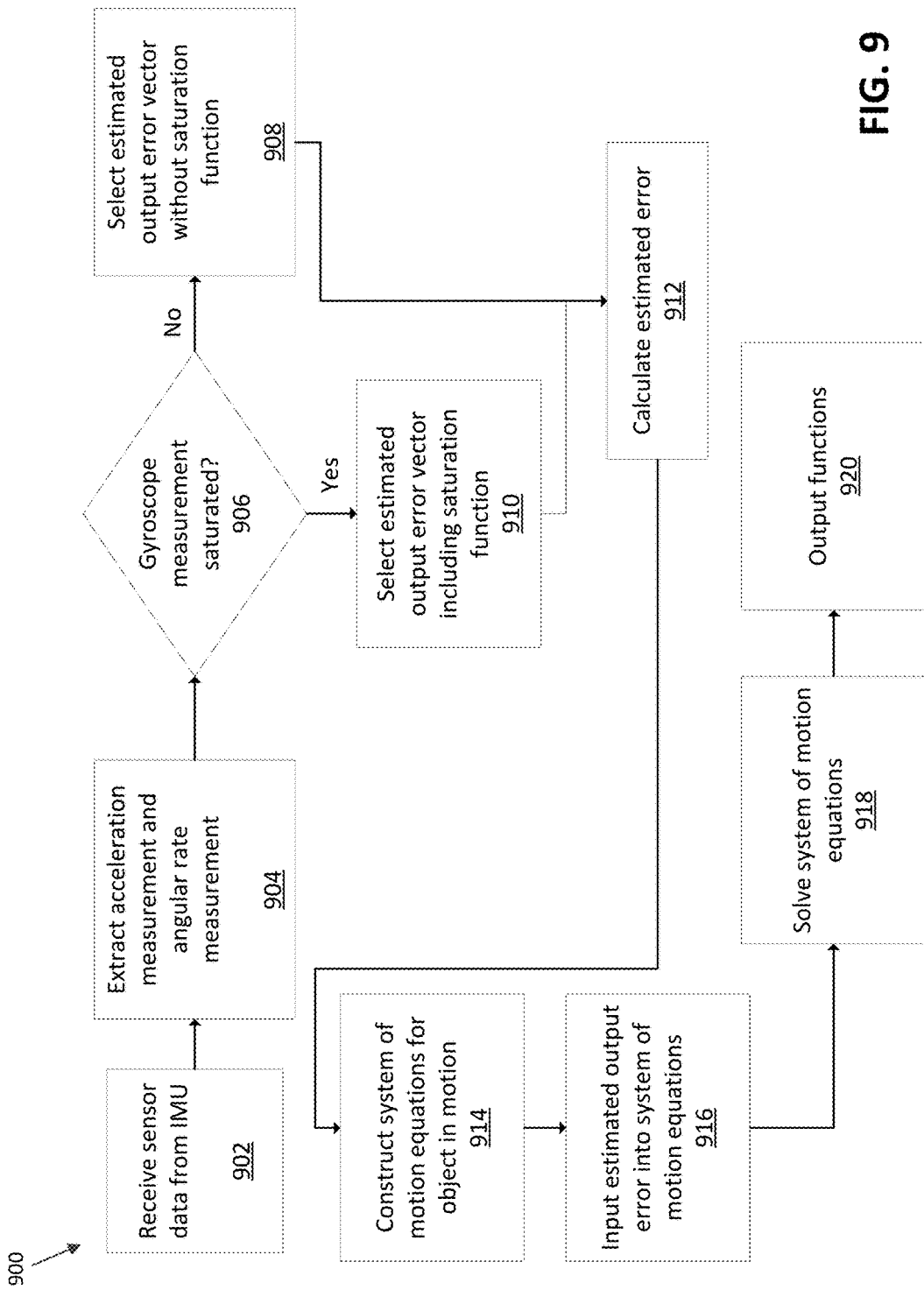
FIG. 9 is an illustrative flowchart diagram for determining functions to describe a golf swing motion, according to one or more aspects described herein.

FIG. 9 schematically depicts a flowchart diagram 900 for determining one or more functions that describe a golf swing motion between a first time instant and a second time instant. The following processes may be executed by, among others, processing circuit 206. Accordingly, one or more processes may be executed to receive sensor data. This sensor data may be received from IMU 200, and include one or both of accelerometer data and gyroscope data. Additionally, data may be received from IMU 200 between a first time instant and a second time instant, as previously described in this disclosure. Further, these one or more processes to receive the sensor data from the inertial measurement unit, such as IMU 200, may be executed at block 902 of flowchart 900.

Received sensor data may be processed to parse out, or extract and differentiate acceleration data from gyroscope data. Accordingly, data associated with an accelerometer may include an identifier, such as, among others, a specific sequence of bits added to a stream, or packet, of raw sensor data that identifies the data as accelerometer data. Additionally or alternatively, sensor data from an accelerometer may be received on a dedicated communication channel, such as a specific communication frequency, or specific physical port. Similarly, data received from a gyroscope may include a different identifier. It should be appreciated that any methods for identifying different data streams may be utilized without departing from the scope of these disclosures. Further, the described accelerometer may include data from three accelerometers aligned with three orthogonal axes such that each of the three accelerometers is associated with a different identifier. In the same way, the described gyroscope may include data from three gyroscopes about the same three orthogonal axes, and such that each of the three gyroscopes is associated with a different identifier. These one or more processes to extract acceleration data, otherwise referred to as an acceleration measurement, and gyroscope data, otherwise referred to as an angular rate measurement, may be executed at block 904 of flowchart 900.

One or more processes may be executed to analyze the received gyroscope data, and to determine whether a gyroscope saturation event has occurred. A gyroscope saturation event may be identified as a sensor reading from a gyroscope that has a value equal to an upper limit of a range of angular velocities that the gyroscope is capable of measuring. It will be readily understood that this upper limit may vary with the specific type of gyroscope used, but that this disclosure may utilized to identify a gyroscope saturation event for any gyroscope type, without departing from these disclosures. These one or more processes to identify, from the received angular rate measurement data, a gyroscope saturation event, may be executed at decision block 906. Accordingly, if no gyroscope saturation event is identified from the received sensor data, flowchart 900 may proceed to block 908.

In one example, one or more processes may be executed to select an estimated output error vector that does not include a saturation function. As such, this estimated output error vector that does not include a saturation function may correspond to Equation 1-Equation 31.6, as presented below. These one or more processes to select the estimated output error vector that does not include a saturation function may be executed at block 908 of flowchart 900.

If a gyroscope saturation event is identified at decision block 906, flowchart 900 may proceed to block 910. Accordingly, in another example, one or more processes may be executed to select an estimated output error vector that includes a saturation function. This estimated output error vector that includes a saturation function may correspond to Equation 30.1 Equation 30.6, as presented below. Accordingly, one or more processes to select the estimated output error vector that includes a saturation function may be executed at block 910 of flowchart 900.

The estimated output error vector that accounts for gyroscope saturation, and corresponding to Equations 30.1-30.6, or the estimated output error vector that does not account for gyroscope saturation, and corresponding to Equations 31.1-31.6, may be utilized to calculate an estimated error. Accordingly, one or more processes may be executed to calculate an estimated error using either Equations 30.1-30.6 or Equations 31.1-31.6 at block 912 of flowchart 900.

A system of motion equations may be constructed to describe a motion of a golf club, e.g. a motion of a golf club head, between a first time instant and a second time instant corresponding to instances in time during a golf swing motion. The system of motion equations may not require an input force or an input torque to the golf club to be known. Accordingly, the system of motion equations may be constructed with methodology that utilizes an unknown input observer. Additionally, the system of motion equations may take account of, or compensate for, gyroscope bias without using static leveling, and may calculate angular rates when a gyroscope has saturated (when using the system of motion equations with Equations 30.1-30.6). Accordingly, the system of motion equations may correspond to Equations 1-29, described in further detail below. In one example, construction of the system of motion equations may include one or more processes to define multiple variables, including allocation of memory corresponding to the differential equations described by Equation 1-Equation 29 such that they are solvable by numerical methods implemented by a processor, such as processing circuit 206. Accordingly, one or more processes to construct a system of motion equations may be executed at block 914 of flowchart 900.

The system of motion equations may include Equation 1 to Equation 29, as described below. These equations represent a system of coupled ordinary differential equations. Accordingly, solutions, in the form of functions, for each of Equations 1-29 may be found by simultaneously solving the Equations 1-29 using one or more solver processes. In particular, an integrator process may be executed on each of Equations 1-29. Those of ordinary skill in the art will recognize various examples of solver processes for solving systems of coupled differential equations. As such, Equations 1-29 may be simultaneously solved by any solver processor known in the art, without departing from the scope of these disclosures. Additionally, given the complexity of the twenty-nine coupled equations, as well as the speed at which an analysis of a golf swing is to be carried out (in one example, analysis of a golf swing may be available for review by the golfer/user directly following a golf shot), it will be readily understood that Equations 1-29 will be solved by a high-frequency/ high clock speed processor, such as that described in relation to processing circuit 206.

Described below are the twenty-nine coupled ordinary differential equations that may be solved to describe the motion of the golf swing, based on inertial measurement unit (e.g. IMU 200) data, without knowledge of input force, torque, or gyroscope bias:

$$\frac{d\hat{\omega}_x}{dt} = \frac{\hat{\zeta}_x}{J_x} - \frac{(J_z - J_y)}{J_x}\hat{\omega}_y\hat{\omega}_z + L_1\bar{e} \quad \text{(Equation 1)}$$

$$\frac{d\hat{\omega}_y}{dt} = \frac{\hat{\zeta}_y}{J_y} - \frac{(J_x - J_z)}{J_y}\hat{\omega}_x\hat{\omega}_z + L_2\bar{e} \quad \text{(Equation 2)}$$

$$\frac{d\hat{\omega}_z}{dt} = \frac{\hat{\zeta}_z}{J_z} - \frac{(J_y - J_x)}{J_z}\hat{\omega}_x\hat{\omega}_y + L_3\bar{e} \quad \text{(Equation 3)}$$

$$\frac{d\hat{\zeta}_{x_1}}{dt} = \hat{\zeta}_{x_2} + L_4\bar{e} \quad \text{(Equation 4)}$$

$$\frac{d\hat{\zeta}_{x_2}}{dt} = \hat{m}_{\zeta_x}\hat{\zeta}_{x_1} + L_5\bar{e} \quad \text{(Equation 5)}$$

$$\frac{d\hat{m}_{\zeta_x}}{dt} = L_6\hat{\zeta}_{x_1}\bar{e} \quad \text{(Equation 6)}$$

$$\frac{d\hat{\zeta}_{y_1}}{dt} = \hat{\zeta}_{y_2} + L_7\bar{e} \quad \text{(Equation 7)}$$

$$\frac{d\hat{\zeta}_{y_2}}{dt} = \hat{m}_{\zeta_y}\hat{\zeta}_{y_1} + L_8\bar{e} \quad \text{(Equation 8)}$$

$$\frac{d\hat{m}_{\zeta_y}}{dt} = L_9\hat{\zeta}_{y_1}\bar{e} \quad \text{(Equation 9)}$$

$$\frac{d\hat{\zeta}_{z_1}}{dt} = \hat{\zeta}_{z_2} + L_{10}\bar{e} \quad \text{(Equation 10)}$$

-continued $$\frac{d\hat{\zeta}_{z2}}{dt} = \hat{m}_{\zeta_z}\hat{\zeta}_{z1} + L_{11}\overline{e} \quad \text{(Equation 11)}$$

$$\frac{d\hat{m}_{\zeta_z}}{dt} = L_{12}\hat{\zeta}_{z1}\overline{e} \quad \text{(Equation 12)}$$

$$\frac{d\hat{B}_x}{dt} = L_{13}\overline{e} \quad \text{(Equation 13)}$$

$$\frac{d\hat{B}_y}{dt} = L_{14}\overline{e} \quad \text{(Equation 14)}$$

$$\frac{d\hat{B}_z}{dt} = L_{15}\overline{e} \quad \text{(Equation 15)}$$

$$\frac{d\hat{x}_2}{dt} = \hat{\omega}_z\hat{y}_2 - \hat{\omega}_y\hat{z}_2 - \sin(\hat{\theta})g + \frac{\hat{f}_{x_1}}{(\text{mass})} + L_{16}\overline{e} \quad \text{(Equation 16)}$$

$$\frac{d\hat{y}_2}{dt} = -\hat{\omega}_z\hat{x}_2 + \hat{\omega}_x\hat{z}_2 + \sin(\hat{\phi})\cos(\hat{\theta})g + \frac{\hat{f}_{y_1}}{(\text{mass})} + L_{17}\overline{e} \quad \text{(Equation 17)}$$

$$\frac{d\hat{z}_2}{dt} = \hat{\omega}_y\hat{x}_2 - \hat{\omega}_x\hat{y}_2 + \cos(\hat{\theta})\cos(\hat{\phi})g + \left(\frac{\hat{f}_{z_1}}{(\text{mass})} - g\right) + L_{18}\overline{e} \quad \text{(Equation 18)}$$

$$\frac{d\hat{f}_{x_1}}{dt} = \hat{f}_{x_2} + L_{19}\overline{e} \quad \text{(Equation 19)}$$

$$\frac{d\hat{f}_{x_2}}{dt} = -\hat{m}_{f_x} + L_{20}\overline{e} \quad \text{(Equation 20)}$$

$$\frac{d\hat{m}_{f_x}}{dt} = L_{21}\hat{f}_{x_1}\overline{e} \quad \text{(Equation 21)}$$

$$\frac{d\hat{f}_{y_1}}{dt} = \hat{f}_{y_2} + L_{22}\overline{e} \quad \text{(Equation 22)}$$

$$\frac{d\hat{f}_{y_2}}{dt} = \hat{m}_{f_y}\hat{f}_{y_1} + L_{23}\overline{e} \quad \text{(Equation 23)}$$

$$\frac{d\hat{m}_{f_y}}{dt} = L_{24}\hat{f}_{y_1}\overline{e} \quad \text{(Equation 24)}$$

$$\frac{d\hat{f}_{z_1}}{dt} = \hat{f}_{z_2} + L_{25}\overline{e} \quad \text{(Equation 25)}$$

$$\frac{d\hat{f}_{z_2}}{dt} = -\hat{m}_{f_z}\hat{f}_{z_1} + L_{26}\overline{e} \quad \text{(Equation 26)}$$

$$\frac{d\hat{m}_{f_z}}{dt} = L_{27}\hat{f}_{z_1}\overline{e} \quad \text{(Equation 27)}$$

$$\frac{d\hat{\phi}}{dt} = \hat{\omega}_x + \hat{\omega}_y\sin(\hat{\phi})\tan(\hat{\theta}) + \hat{\omega}_z\cos(\hat{\phi})\tan(\hat{\theta}) + L_{28}\overline{e} \quad \text{(Equation 28)}$$

$$\frac{d\hat{\theta}}{dt} = \hat{\omega}_y\cos(\hat{\phi}) + \hat{\omega}_z\sin(\hat{\phi}) + L_{29}\overline{e} \quad \text{(Equation 29)}$$

With regard to Equations 1-29 above: subscripts x, y, and z correspond to three mutually-perpendicular axes, subscripts $x_1$, $y_1$, and $z_1$ correspond to displacements along the x, y, and z axes (units: m), subscripts $x_2$, $y_2$, and $z_2$ correspond to derivatives with respect to the x, y, and z axes (velocities) (units: m s$^{-1}$), ω=angular rate (units: rad s$^{-1}$), $\hat{\omega}$=angular rate estimate (units: rad s$^{-1}$), J=moment of inertia (units: kg·m$^2$), $\hat{\zeta}$=torque estimate (units: N·m), $\hat{m}_\zeta$=torque frequency estimate ($\hat{m}_{\zeta_x}$=torque frequency estimate about the x-axis, $\hat{m}_{\zeta_y}$=torque frequency estimate about the y-axis, $\hat{m}_{\zeta_z}$=torque frequency estimate about the z-axis) (units: rad s$^{-1}$), B=angular rate bias (units: rad s$^{-1}$), $\hat{B}$=angular rate bias estimate (units: rad s$^{-1}$), $\hat{x}_2$=velocity estimate along x-axis (units: m s$^{-1}$), $\hat{y}_2$=velocity estimate along y-axis (units: m·s$^{-1}$), $\hat{z}_2$=velocity estimate along z-axis (units: m·s$^{-1}$), $\hat{f}$=force estimate (units: N), $\hat{m}_f$=force frequency estimate (units: rad·s$^{-1}$), $\hat{\phi}$=pitch estimate (units: rad), $\hat{\theta}$=roll estimate (units: rad), g=acceleration due to gravity (9.81 m·s$^{-2}$), (mass)=mass of object in motion (in one example, this mass may be set equal to a golf club head mass, or a mass of the golf club head in combination with a shaft and a grip, among others) (units: kg), $L_1$-$L_{29}$=twenty-nine unknown design gains.

Accordingly, the twenty-nine unknown design gains, $L_1$-$L_{29}$, may be constant values, or may be functions, without departing from the scope of this disclosure.

Equations 1-29 include an estimated output error, $\overline{e}$, as described in further detail in relation to Equations 30.1-30.6 and 31.1-31.6.

The coupled system of Equations 1-29 may be solved to provide 29 functions with respect to time. Included in these results will be functions describing input force, input torque, roll angle, and pitch angle between a first time instant and a second time instant corresponding to, in one example, a portion of a golf swing motion. Equations 1-29 provide these results using acceleration data (e.g. linear accelerometer data along three orthogonal axes) and gyroscope data (e.g. angular rate data about the three orthogonal axes). The initial conditions for pitch and roll angles may be unknown. Similarly, the input force and torque to the golf club from the user may be unknown. As such, Equations 1-29 may be constructed using Unknown Input Observer methodology. This Unknown Input Observer methodology utilizes the twenty-nine unknown design gains, $L_1$-$L_{29}$, and the estimated output error, $\overline{e}$, as described in further detail throughout this disclosure.

In one example, Equations 1, 2, 3, 16, 17, 18, 28, and 29 include well-known equations of motion for a rotating and translating body, but augmented with Unknown Input Observer mismatch terms and estimated output errors: $L_1\overline{e}$, $L_2\overline{e}$, $L_3\overline{e}$, $L_{16}\overline{e}$, $L_{17}\overline{e}$, $L_{18}\overline{e}$, $L_{28}\overline{e}$, and $L_{29}\overline{e}$, respectively.

Equations 4, 5, and 6 describe an estimate of torque as a sinusoid with an unknown frequency. As such $$\frac{d\hat{\zeta}_{x_1}}{dt}$$

in Equation 4 is a first derivative of a sine wave, while $$\frac{d\hat{\zeta}_{x_2}}{dt}$$

is a second derivative of a sine wave. The frequency of this torque estimate is assumed to be constant, hence the derivative of this frequency, per $$\frac{d\hat{m}_{\zeta_x}}{dt}$$

from Equation 6, is assumed to equal zero, but augmented with the mismatch term, sine wave estimate, and estimated output error; $L_6\hat{\zeta}_{x_1}\overline{e}$ from Equation 6. Accordingly, Equations 4, 5, and 6 are utilized to calculate an estimate of the amplitude and frequency of the sine wave that represents torque about the x-axis. Similarly, Equations 7, 8 and 9 are utilized to calculate an estimate of the amplitude and frequency of the sine wave that represents torque about the y-axis. Further, Equations 10, 11, and 12 are utilized to calculate an estimate of the amplitude and frequency of the sine wave that represents torque about the z-axis.

Conventionally, and in contrast to the systems and methodology described in relation to Equations 1-29 above, in order to calculate a motion of a body, such as a golf club head moving through a golf swing motion, analysis may require initial conditions to be found using a process of static leveling. This may include resting a gyroscope (e.g. an IMU including a gyroscope) perfectly still such that one or more gyroscope biases can be measured and compensated for. Additionally, this process may allow for initial conditions for orientation (pitch and roll) to be found. In contrast to this conventional methodology, this disclosure, including Equations 1-29, does not require initial conditions for orientation of, for example, IMU 200, and may estimate gyroscope bias without requiring the IMU 200 to remain stationary for a period. As such, given that, in one example, Equations 1-29 will be utilized to analyze a golf swing during a round of golf (i.e. outside of controlled laboratory conditions), the described systems and methods herein may offer an advantage of not requiring a golf club to remain perfectly still in order to analyze a golf swing.

Further to the above, for those conventional systems that may utilize static leveling, the differential equations to be solved to describe the motion of a golf club head may include Equations 1, 2, 3, 16, 17, 18, 28, and 29 without the Unknown Input Observer mismatch terms and estimated output errors: $L_1\bar{e}$, $L_2\bar{e}$, $L_3\bar{e}$, $L_{16}\bar{e}$, $L_{17}\bar{e}$, $L_{18}\bar{e}$, $L_{28}\bar{e}$, and $L_{29}\bar{e}$, respectively. However, and as previously described, this methodology may be impractical for one or more real-world applications, such as those disclosures described herein, which allow for calculation of, among others, input force, input torque, roll angle and pitch angle of a golf club based on accelerometer and gyroscope data alone, and accounting for gyroscope bias without requiring a period of rest for an IMU 200 outputting the accelerometer and gyroscope data.

A gyroscope may output a biased reading that may drift with, among others, time and/or temperature. However, the rate of drift of a bias error from a gyroscope may be approximated as being equal to zero. As such, a derivative of a bias estimate may be equal to zero, as utilized in Equations 13, 14, and 15, with the addition of the Unknown Input Observer mismatch terms $L_{13}\bar{e}$, $L_{14}\bar{e}$, and $L_{15}\bar{e}$.

The coupled system of motion equations may estimate force as a sinusoid with an unknown, but constant frequency. Accordingly, Equations 19, 20, and 21 are similar to Equations 4, 5, and 6 described above with regard to estimation of a torque amplitude and frequency. Specifically, Equations 19, 20, and 21 are utilized to estimate a sinusoidal force amplitude and frequency associated with the x-axis. Similarly, Equations 22, 23 and 24 estimate a sinusoidal force amplitude and frequency associated with the y-axis, and Equations 25, 26, and 27 estimate a sinusoidal force amplitude and frequency associated with the z-axis.

[95] In view of the above description it will be appreciated that Equations 1-29 form a system of coupled equations to be solved simultaneously as a group, and made up of equations constructed for the specific application of calculating functions of unknown force, torque, pitch angle and roll angle, using received input data from an IMU, such as IMU 200, and compensating for gyroscope bias without requiring static leveling. Input data received from IMU 200 may include, but not be limited to, numbers (communicated as, in one example, one or more sequences of bits) that correspond to one or more linear accelerations and/or angular velocities associated with three orthogonal (mutually-perpendicular) axes. In one example, Equations 1-29 may be represent a full-order coupled system of motion equations, and utilizing a full-order unknown input observer.

In another example, a reduced-order unknown input observer may be utilized to analyze the motion of a golf club head, and using less than the complete system of Equations 1-29. For example, a reduced order unknown input observer may utilize equations associated with a single axis (x-axis, y-axis, or z-axis), among others.

In one example, the term used in Equation 1 to Equation 29 above may be an estimated output error, and include a saturation function. As such, $\bar{e}$ may be a 6×1 vector of the form:

$$\bar{e}(1) = \text{sat}(\omega_x + B_x) - \text{sat}(\hat{\omega}_x + \hat{B}_x) \quad \text{(Equation 30.1)}$$

$$\bar{e}(2) = \text{sat}(\omega_y + B_y) - \text{sat}(\hat{\omega}_y + \hat{B}_y) \quad \text{(Equation 30.2)}$$

$$\bar{e}(3) = \text{sat}(\omega_z + B_z) - \text{sat}(\hat{\omega}_z + \hat{B}_z) \quad \text{(Equation 30.3)}$$

$$\bar{e}(4) = a_x - \hat{a}_x \quad \text{(Equation 30.4)}$$

$$\bar{e}(5) = a_y - \hat{a}_y \quad \text{(Equation 30.5)}$$

$$\bar{e}(6) = a_z - \hat{a}_z \quad \text{(Equation 30.6)}$$

In another example, the term used in Equation 1 to Equation 29 above may be an estimated output error that does not include a saturation function. As such, $\bar{e}$ may be a 6×1 vector of the form:

$$\bar{e}(1) = (\omega_x + B_x) - (\hat{\omega}_x + \hat{B}_x) \quad \text{(Equation 31.1)}$$

$$\bar{e}(2) = (\omega_y + B_y) - (\hat{\omega}_y + \hat{B}_y) \quad \text{(Equation 31.2)}$$

$$\bar{e}(3) = (\omega_z + B_z) - (\hat{\omega}_z + \hat{B}hd\ z) \quad \text{(Equation 31.3)}$$

$$\bar{e}(4) = a_x - \hat{a}_x \quad \text{(Equation 31.4)}$$

$$\bar{e}(5) = a_y - \hat{a}_y \quad \text{(Equation 31.5)}$$

$$\bar{e}(6) = a_z - \hat{a}_z \quad \text{(Equation 31.6)}$$

With regards to equations 30.1-30.6 and equations 31.1-31.6 above: $\omega_x$, $\omega_y$, and $\omega_z$ are measured angular rates about the x-, y-, and z-axis, respectively (units: rad·s$^{-1}$); $\hat{\omega}_x$, $\hat{\omega}_y$, and $\hat{\omega}_z$ are angular rate estimates about the x-, y-, and z-axis, respectively (units: rad s$^{-1}$); $a_x$, $a_y$, and $a_z$ are measured linear accelerations along the x-, y-, and z-axis, respectively (units: m s$^{-2}$); $\hat{a}_x$, $\hat{a}_y$, and $\hat{a}_z$ are estimated linear accelerations along the x-, y-, and z-axis, respectively (units: m·s$^{-2}$); $B_x$, $B_y$, and $B_z$ are unknown angular rate biases about the x-, y-, and z-axis, respectively (units: rad s$^{-1}$); and $\hat{B}_x$, $\hat{B}_y$, and $\hat{B}_z$ are angular rate bias estimates about the x-, y-, and z-axis, respectively (units: rad·s$^{-1}$).

With regard to Equations 30.1, 30.2 and 30.3 described above, the "sat( )" element may be utilized to address gyroscope saturation (see, e.g. block 910 of flowchart 900). This "sat( )" element may be implemented as type of "if-else" process that sets the value to be equal to the highest output possible from a gyroscope if the value in parentheses is above that highest output, or otherwise sets the value equal to the output value from the gyroscope.

In one implementation, the data received from IMU 200 may be utilized in the estimated output error, $\bar{e}$, as described in Equations 30.1-30.6 or 31.1-31.6. Accordingly, one or more processes may be executed to estimate the output error, and to input the estimated output error into the system of motion equations (Equations 1-29) at block 916 of flowchart 900.

The coupled system of motion equations (Equations 1-29) may be simultaneously solved using any appropriate solver processes, without departing from the scope of these disclosures, as described above. These one or more processes for solving the system of motion equations may be executed at block 918 of flowchart 900. In certain implementations, one or more solver processes that may be utilized to solve the coupled system of ordinary differential equations (Equations 1-29) may include Runge-Kutta, Adams, Rosenbrock, Trapezoidal Rule, Dorman-Prince, or Euler solver processes, among others. Further, when solving Equations 1-29, a user may specify convergence criteria, which may include one or more threshold values corresponding to an error between a measured and an estimated signal. As such, Equations 1-29 may be determined to have converged when the difference (error) between measured (from sensors, such as IMU 200) and estimated signals (from Equations 1-29) is less than a threshold. Accordingly, such a threshold may have any value, without departing from the scope of these disclosures.

As previously described, the system of motion equations may be solved to provide twenty-nine output functions. Among these solutions may be functions describing input force, input torque, roll angle, and/or pitch angle of, in one example, a golf club head between a first time instant and a second time instant during a golf swing motion. As such, one or more processes may be executed to output functions describing input force, input torque, roll angle, and/or pitch angle as a function of time at block 920 of flowchart 900.

Figure 10:
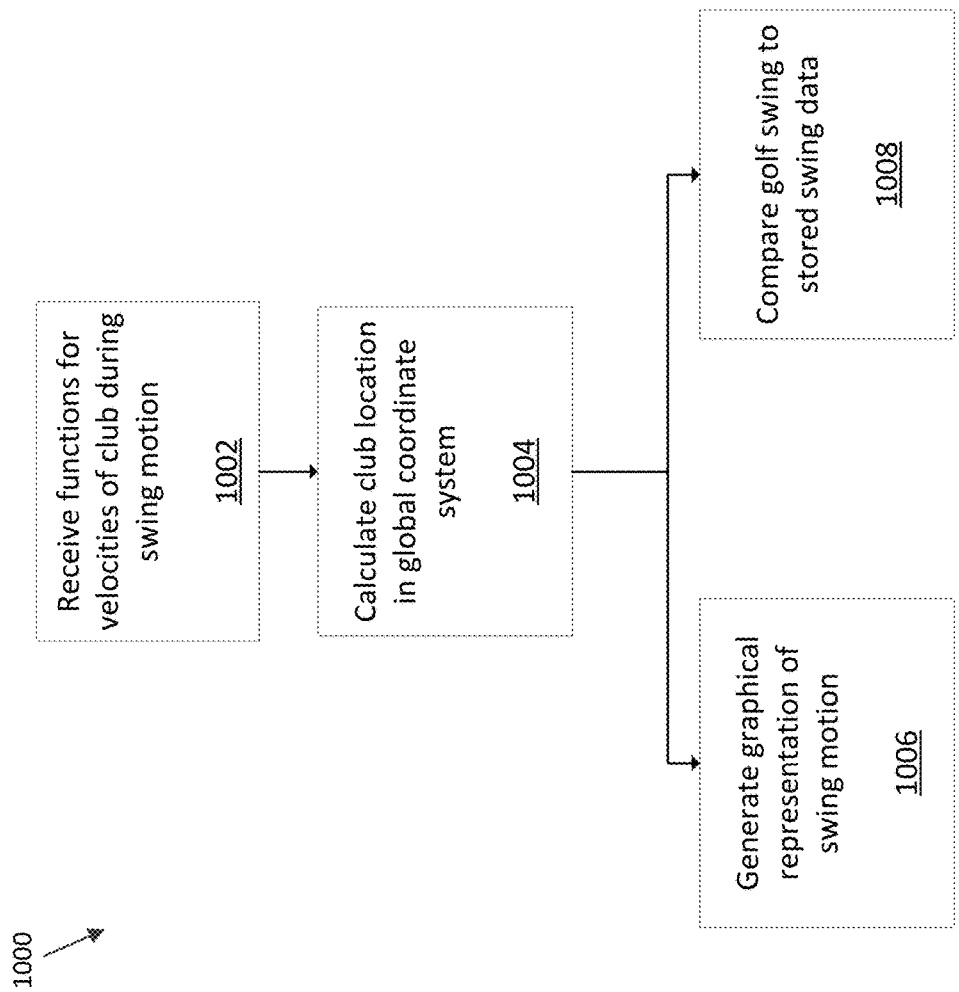
FIG. 10 is an illustrative flowchart diagram for determining a location of a golf club in a global coordinate system, according to one or more aspects described herein.

Flowchart 900 may provide one or more output functions describing input force and input torque to a golf club head during a golf swing motion (i.e. functions with respect to time between a first instant and a second instant). Additionally, flowchart 900 may output functions of roll angle and pitch angle. FIG. 10 schematically depicts a flowchart diagram 1000 for determining a location of a golf club in a global coordinate system, and for generating a graphical representation of the golf swing motion. Accordingly, one or more functions describing velocities of the golf club head may be received by a computing device (e.g. processing circuit 206). These one or more functions describing velocities may be the output functions of one or more of Equations 16, 17, and 18. These functions may have the general form of $\hat{x}_2 = f_1(t)$, $\hat{y}_2 = f_2(t)$, and $\hat{z}_2 = f_3(t)$, where $f_1$, $f_2$, and $f_3$, generally represent functions with respect to time. As such, one or more processes may be executed to receive one or more of functions $f_1$, $f_2$, and $f_3$ at block 1002 of flowchart 1000.

In one example, the functions describing velocities of the golf club head (e.g. functions $f_1$, $f_2$, and $f_3$) may utilize Euler angles (e.g. roll and pitch angles). It may be desirable to calculate the position of the golf club head in a global coordinate system (otherwise referred to as a world coordinate system). As such, this calculation may integrate each of the following equations 32-34:

$$\frac{d\hat{x}_1}{dt} = \hat{x}_2 \quad \text{(Equation 32)}$$

$$\frac{d\hat{y}_1}{dt} = \hat{y}_2 \quad \text{(Equation 33)}$$

$$\frac{d\hat{z}_1}{dt} = \hat{z}_2 \quad \text{(Equation 34)}$$

With regards to equations 32-34 above: $\hat{x}_1$ is an estimate of a position along an x-axis of the global coordinate system (units: m), $\hat{y}_1$ is an estimate of a position along a y-axis of the global coordinate system (units: m), and $\hat{z}_1$ is an estimate of a position along a z-axis of the global coordinate system (units: m).

It is noted that Equations 32, 33, and 34 are not coupled to Equations 1-29 such that they do not need to be solved simultaneously with Equations 1-29.

Accordingly, one or more processes may be executed to calculate a golf club location in a global coordinate system, and using Equations 32-34, at block 1004 of flowchart 1000.

A graphical representation of a golf swing motion may be generated for display (e.g. for display using output device 323, which may be a monitor display of device 104 or device 106). In one example, the calculated golf club location in the global coordinate system may be utilized to plot a graphical representation of the golf swing. Those of ordinary skill in the art will recognize specific processes for generating a graphical display, as well as specific hardware elements (GPUs, and the like), any of which may be utilized with the disclosures described herein. Further, various examples of specific graphics, such as swing path coloring and shading, among others, may be utilized without departing from these disclosures. As such, one or more processes for generation of a graphical representation of a swing motion may be executed at block 1006 of flowchart 1000. In one example, the calculated golf swing data may be utilized to compare a user's golf swing to a database of stored swing data. This stored swing data may include model swing data. As such, in one example, this model swing data may be based upon a golf swing of a professional level golfer, among others. Accordingly, the model swing data may be compared to the calculated swing data. The comparison may indicate one or more differences between the model swing data and the calculated swing data such that a user may be provided with feedback about his/her swing. However, those of ordinary skill in the art will recognize various implementations utilizing the calculated golf swing data from at least Equation 1-29 to provide feedback to a user, any of which may be utilized without departing from the scope of the disclosures described herein. In one implementation, one or more processes for comparison of golf swing data to a stored golf swing data may be executed at block 1008 of flowchart 1000.

Further to the description of Equations 1-29, while functions for a pitch estimate ($\hat{\phi}$), and a roll estimate ($\hat{\theta}$) may be calculated using the system of coupled ordinary differential equations (Equations 1-29), an equation for a yaw estimate ($\hat{\psi}$) (units: rad) is not included in Equations 1-29. Accordingly, it will be readily understood that while the equations for the pitch and roll estimates are coupled to one or more of the other variables in Equations 1-29 (the initial conditions of pitch estimate and roll estimate are dependent on gravity, for example), a yaw estimate is not coupled to one or more of Equations 1-29 in the same manner. Accordingly, a function estimating yaw ($\hat{\psi}$) may be calculated using Equation 35 below:

$$\frac{d\hat{\psi}}{dt} = \hat{\omega}_y \frac{\sin(\hat{\phi})}{\cos(\hat{\theta})} + \hat{\omega}_z \frac{\cos(\hat{\phi})}{\cos(\hat{\theta})} \quad \text{(Equation 35)}$$

The initial condition for yaw (e.g. yaw estimate ($\hat{\psi}$)) may be arbitrarily defined, or may be user defined (e.g. it is not dependent on gravity). Further, in one implementation, Equation 35 should not be integrated until convergence criteria of the coupled system of equations (Equations 1-29) has been met (e.g. the error between the measured and estimated signals is less than a threshold).

Figure 11:
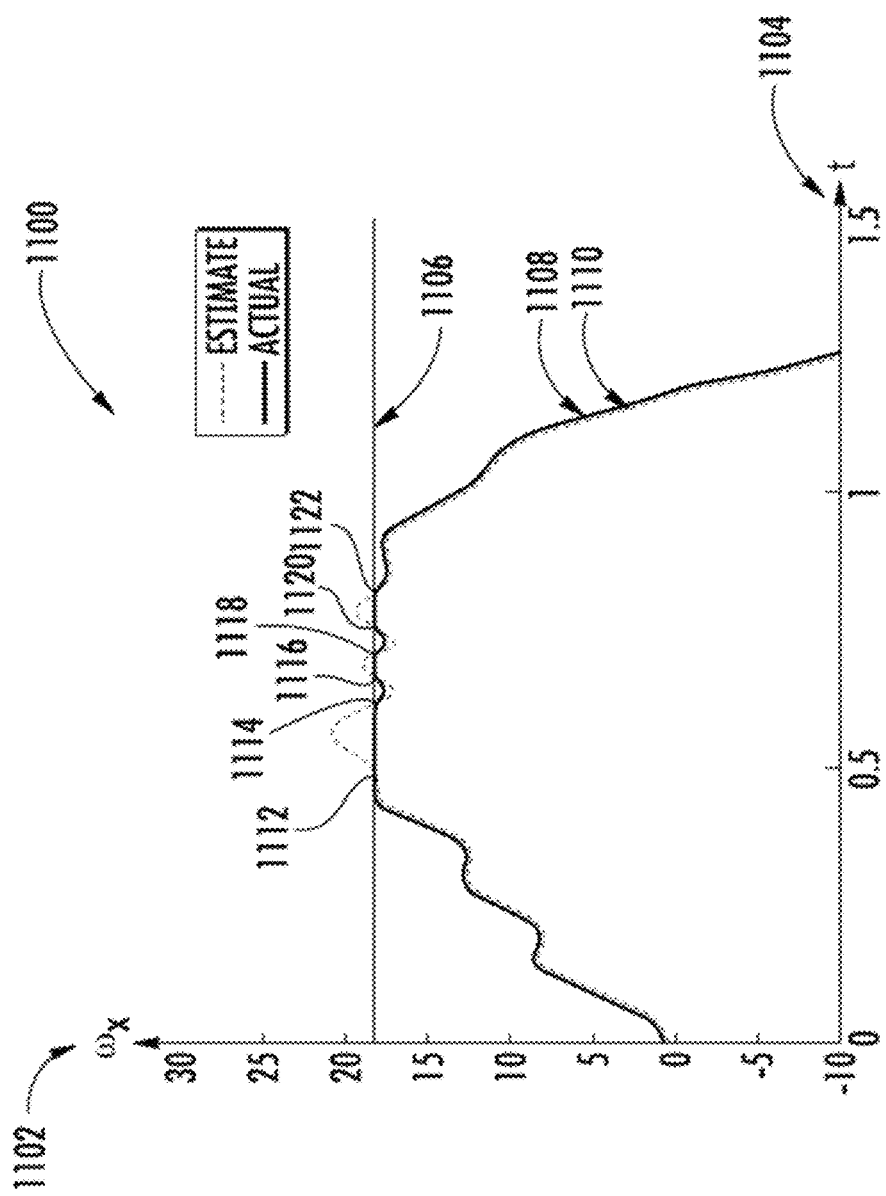
FIG. 11 depicts output results of one validation test of the systems and methodology described in relation to Equation 1-29.

FIG. 11 depicts the results of one validation test of the systems and methodology described in relation to Equations 1-29. In particular, FIG. 11 depicts a plot of angular rate about the x-axis ($\omega_x$)(units: rad s$^{-1}$) on axis 1102 versus time (units: s) on axis 1104. Line 1106 represents a saturation value above which the gyroscope is incapable of measuring.

Accordingly, graph 1108 plots the actual angular rate values received from the gyroscope. As such, the actual angular rate data saturates between points 1112 and 1114, between points 1116 and 1118, and again between points 1120 and 1122.

Graph 1110, as depicted in FIG. 11 is plotted using data calculated using Equations 1-29. Accordingly, from FIG. 11 it is apparent that there is a high goodness of fit between the actual data in graph 1108, and the estimated data of graph 1110. Additionally, graph 1110 depicts the use of the saturation functionality offered in Equations 30.1-30.6, and compensates for the saturated output from the gyroscope between points 1112 and 1114, between points 1116 and 1118, and again between points 1120 and 1122.

The various implementations of this disclosure are described in relation to golf swing analysis, whereby a system of coupled equations (Equations 1-29) may be utilized to, among others, calculate a position of a golf club throughout a golf swing motion, as well as to calculate functions representing an unknown input force and torque. Further, the coupled equations may be utilized to compensate for gyroscope bias and saturation, without requiring a period of static leveling. However, it should be understood that the systems and methods described herein may be utilized with an IMU 200 that may be integrated into a generalized object in motion. In various examples, this object in motion may be an item of sporting equipment, such as a tennis racket or other racket, a baseball bat, a hockey stick, a lacrosse stick, or a sports ball, among others. Further the various disclosures described herein may be utilized in non-sports-related applications, including any object in motion in which an IMU, such as IMU 200, is employed.

The various embodiments described herein may be implemented by general-purpose or specialized computer hardware. In one example, the computer hardware may comprise one or more processors, otherwise referred to as microprocessors, having one or more processing cores configured to allow for parallel processing/execution of instructions. As such, the various disclosures described herein may be implemented as software coding, wherein those of skill in the art will recognize various coding languages that may be employed with the disclosures described herein. Additionally, the disclosures described herein may be utilized in the implementation of application-specific integrated circuits (ASICs), or in the implementation of various electronic components comprising conventional electronic circuits (otherwise referred to as off-the-shelf components). Furthermore, those of ordinary skill in the art will understand that the various descriptions included in this disclosure may be implemented as data signals communicated using a variety of different technologies and processes. For example, the descriptions of the various disclosures described herein may be understood as comprising one or more streams of data signals, data instructions, or requests, and physically communicated as bits or symbols represented by differing voltage levels, currents, electromagnetic waves, magnetic fields, optical fields, or combinations thereof.

One or more of the disclosures described herein may comprise a computer program product having computer-readable medium/media with instructions stored thereon/therein that, when executed by a processor, are configured to perform one or more methods, techniques, systems, or embodiments described herein. As such, the instructions stored on the computer-readable media may comprise actions to be executed for performing various steps of the methods, techniques, systems, or embodiments described herein. Furthermore, the computer-readable medium/media may comprise a storage medium with instructions configured to be processed by a computing device, and specifically a processor associated with a computing device. As such, the computer-readable medium may include a form of persistent or volatile memory such as a hard disk drive (HDD), a solid state drive (SSD), an optical disk (CD-ROMs, DVDs), tape drives, floppy disk, ROM, RAM, EPROM, EEPROM, DRAM, VRAM, flash memory, RAID devices, remote data storage (cloud storage, and the like), or any other media type or storage device suitable for storing data thereon/therein. Additionally, combinations of different storage media types may be implemented into a hybrid storage device. In one implementation, a first storage medium may be prioritized over a second storage medium, such that different workloads may be implemented by storage media of different priorities.

Further, the computer-readable media may store software code/instructions configured to control one or more of a general-purpose, or a specialized computer. Said software may be utilized to facilitate interface between a human user and a computing device, and wherein said software may include device drivers, operating systems, and applications. As such, the computer-readable media may store software code/instructions configured to perform one or more implementations described herein.

Those of ordinary skill in the art will understand that the various illustrative logical blocks, modules, circuits, techniques, or method steps of those implementations described herein may be implemented as electronic hardware devices, computer software, or combinations thereof. As such, various illustrative modules/components have been described throughout this disclosure in terms of general functionality, wherein one of ordinary skill in the art will understand that the described disclosures may be implemented as hardware, software, or combinations of both.

The one or more implementations described throughout this disclosure may utilize logical blocks, modules, and circuits that may be implemented or performed with a general-purpose processor, a digital signal processor (DSP), an application-specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, or any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The techniques or steps of a method described in connection with the embodiments disclosed herein may be embodied directly in hardware, in software executed by a processor, or in a combination of the two. In some embodiments, any software module, software layer, or thread described herein may comprise an engine comprising firmware or software and hardware configured to perform embodiments described herein. Functions of a software module or software layer described herein may be embodied directly in hardware, or embodied as software executed by a processor, or embodied as a combination of the two. A software module may reside in RAM memory, flash memory, ROM memory, EPROM memory, EEPROM memory, registers, hard disk, a removable disk, a CD-ROM, or any other form of storage medium known in the art. An example storage medium is coupled to the processor such that the processor can read data from, and write data to, the storage medium. In the alternative, the storage medium may be integral to the processor. The processor and the storage medium may reside in an ASIC. The ASIC may reside in a user device. In the alternative, the processor and the storage medium may reside as discrete components in a user device.

Accordingly, it will be understood that the invention is not to be limited to the embodiments disclosed herein, but is to be understood from the following claims, which are to be interpreted as broadly as allowed under the law.

What is claimed is:

1. An inertial measurement unit, comprising:
    an output device;
    an accelerometer;
    a gyroscope; and
    a non-transitory, computer-readable medium comprising computer-executable instructions that, when executed by a processor, cause a computer device to perform at least:
        receive sensor data between a first time instant and a second time instant from the accelerometer and the gyroscope coupled to an object in motion;
        extract an acceleration measurement and an angular rate measurement from the sensor data;
        construct a system of motion equations, utilizing an unknown input observer, which compensates for gyroscope bias resulting from physical hardware of the gyroscope, for the object in motion;
        calculate an estimated output error using the received sensor data;
        input the estimated output error into a system of motion equations for the object in motion;
        solve the system of motion equations;
        output functions for an input force, an input torque, a roll angle, and a pitch angle from the solved system of motion equations; and
        calculate a series of positions of the object in motion between the first time instant and the second time instant using the output functions.

2. The inertial measurement unit of claim 1, wherein the acceleration measurement comprises acceleration values resolved along three mutually-perpendicular axes and the angular rate measurement comprises angular rate values about the three mutually-perpendicular axes.

3. The inertial measurement unit of claim 2, wherein the estimated output error ($\bar{e}$) is modelled as a 6×1 vector of the form:

$$\bar{e}(1) = (\omega_x + B_x) - (\hat{\omega}_x + \hat{B}_x);$$

$$\bar{e}(2) = (\omega_y + B_y) - (\hat{\omega}_y + \hat{B}_y);$$

$$\bar{e}(3) = (\omega_z + B_z) - (\hat{\omega}_z + \hat{B}_z);$$

$$\bar{e}(4) = a_x - \hat{a}_x;$$

$$\bar{e}(5) = a_y - \hat{a}_y;\ \text{and}$$

$$\bar{e}(6) = a_z - \hat{a}_z,$$

wherein $\omega_x$, $\omega_y$, and $\omega_z$ are measured angular rates along an x-axis, y-axis, and z-axis, respectively; $\hat{\omega}_x$, $\hat{\omega}_y$, and $\hat{\omega}_z$ are angular rate estimates along the x-axis, y-axis, and z-axis, respectively; $a_x$, $a_y$, and $a_z$ are measured linear accelerations along the x-axis, y-axis, and z-axis, respectively; $\hat{a}_x$, $\hat{a}_y$, and $\hat{a}_z$ are estimated linear accelerations along the x-axis, y-axis, and z-axis, respectively, $B_x$, $B_y$, and $B_z$ are measured angular rates biases along the x-axis, y-axis, and z-axis, respectively, and $\hat{B}_x$, $\hat{B}_y$, and $\hat{B}_z$ are angular rate bias estimates along the x-axis, y-axis, and z-axis, respectively.

4. The inertial measurement unit of claim 2, wherein the system of motion equations for the object comprises twenty-nine coupled differential equations of the form:

$$\frac{d\hat{\omega}_x}{dt} = \frac{\hat{\zeta}_x}{J_x} - \frac{(J_z - J_y)}{J_x}\hat{\omega}_y\hat{\omega}_z + L_1\bar{e}; \quad \text{(Equation 1)}$$

$$\frac{d\hat{\omega}_y}{dt} = \frac{\hat{\zeta}_y}{J_y} - \frac{(J_x - J_z)}{J_y}\hat{\omega}_x\hat{\omega}_z + L_2\bar{e}; \quad \text{(Equation 2)}$$

$$\frac{d\hat{\omega}_z}{dt} = \frac{\hat{\zeta}_z}{J_z} - \frac{(J_y - J_x)}{J_z}\hat{\omega}_x\hat{\omega}_y + L_3\bar{e}; \quad \text{(Equation 3)}$$

$$\frac{d\hat{\zeta}_{x_1}}{dt} = \hat{\zeta}_{x_2} + L_4\bar{e}; \quad \text{(Equation 4)}$$

$$\frac{d\hat{\zeta}_{x_2}}{dt} = \hat{m}_{\zeta_x}\hat{\zeta}_{x_1} + L_5\bar{e}; \quad \text{(Equation 5)}$$

$$\frac{d\hat{m}_{\zeta_x}}{dt} = L_6\hat{\zeta}_{x_1}\bar{e}; \quad \text{(Equation 6)}$$

$$\frac{d\hat{\zeta}_{y_1}}{dt} = \hat{\zeta}_{y_2} + L_7\bar{e}; \quad \text{(Equation 7)}$$

$$\frac{d\hat{\zeta}_{y_2}}{dt} = \hat{m}_{\zeta_y}\hat{\zeta}_{y_1} + L_8\bar{e}; \quad \text{(Equation 8)}$$

$$\frac{d\hat{m}_{\zeta_y}}{dt} = L_9\hat{\zeta}_{y_1}\bar{e}; \quad \text{(Equation 9)}$$

$$\frac{d\hat{\zeta}_{z_1}}{dt} = \hat{\zeta}_{z_2} + L_{10}\bar{e}; \quad \text{(Equation 10)}$$

$$\frac{d\hat{\zeta}_{z_2}}{dt} = \hat{m}_{\zeta_z}\hat{\zeta}_{z_1} + L_{11}\bar{e}; \quad \text{(Equation 11)}$$

$$\frac{d\hat{m}_{\zeta_z}}{dt} = L_{12}\hat{\zeta}_{z_1}\bar{e}; \quad \text{(Equation 12)}$$

$$\frac{d\hat{B}_x}{dt} = L_{13}\bar{e}; \quad \text{(Equation 13)}$$

$$\frac{d\hat{B}_y}{dt} = L_{14}\bar{e}; \quad \text{(Equation 14)}$$

$$\frac{d\hat{B}_z}{dt} = L_{15}\bar{e}; \quad \text{(Equation 15)}$$

$$\frac{d\hat{x}_2}{dt} = \hat{\omega}_z\hat{y}_2 - \hat{\omega}_y\hat{z}_2 - \sin(\hat{\theta})g + \frac{\hat{f}_{x_1}}{(\text{mass})} + L_{16}\bar{e}; \quad \text{(Equation 16)}$$

$$\frac{d\hat{y}_2}{dt} = -\hat{\omega}_z\hat{x}_2 + \hat{\omega}_x\hat{z}_2 + \sin(\hat{\phi})\cos(\hat{\theta})g + \frac{\hat{f}_{y_1}}{(\text{mass})} + L_{17}\bar{e}; \quad \text{(Equation 17)}$$

-continued $$\frac{d\hat{z}_2}{dt} = \hat{\omega}_y \hat{x}_2 - \hat{\omega}_x \hat{y}_2 + \cos(\hat{\theta})\cos(\hat{\phi})g + \left(\frac{\hat{f}_{z_1}}{(\text{mass})} - g\right) + L_{18}\overline{e}; \quad \text{(Equation 18)}$$

$$\frac{d\hat{f}_{x_1}}{dt} = \hat{f}_{x_2} + L_{19}\overline{e}; \quad \text{(Equation 19)}$$

$$\frac{d\hat{f}_{x_2}}{dt} = -\hat{m}_{f_y}\hat{f}_{x_1} + L_{20}\overline{e}; \quad \text{(Equation 20)}$$

$$\frac{d\hat{m}_{f_x}}{dt} = L_{21}\hat{f}_{x_1}\overline{e}; \quad \text{(Equation 21)}$$

$$\frac{d\hat{f}_{y_1}}{dt} = \hat{f}_{y_2} + L_{22}\overline{e}; \quad \text{(Equation 22)}$$

$$\frac{d\hat{f}_{y_2}}{dt} = -\hat{m}_{f_y}\hat{f}_{y_1} + L_{23}\overline{e}; \quad \text{(Equation 23)}$$

$$\frac{d\hat{m}_{f_y}}{dt} = L_{24}\hat{f}_{y_1}\overline{e}; \quad \text{(Equation 24)}$$

$$\frac{d\hat{f}_{z_1}}{dt} = \hat{f}_{z_2} + L_{25}\overline{e}; \quad \text{(Equation 25)}$$

$$\frac{d\hat{f}_{z_2}}{dt} = -\hat{m}_{f_z}\hat{f}_{z_1} + L_{26}\overline{e}; \quad \text{(Equation 26)}$$

$$\frac{d\hat{m}_{f_z}}{dt} = L_{27}\hat{f}_{z_1}\overline{e}; \quad \text{(Equation 27)}$$

$$\frac{d\hat{\phi}}{dt} = \hat{\omega}_x + \hat{\omega}_y \sin(\hat{\phi})\tan(\hat{\theta}) + \hat{\omega}_z \cos(\hat{\phi})\tan(\hat{\theta}) + L_{28}\overline{e}; \quad \text{(Equation 28)}$$

and $$\frac{d\hat{\theta}}{dt} = \hat{\omega}_y \cos(\hat{\phi}) + \hat{\omega}_z \sin(\hat{\phi}) + L_{29}\overline{e}, \quad \text{(Equation 29)}$$

wherein subscripts x, y, and z correspond to the three mutually-perpendicular axes, subscripts $x_1$, $y_1$, and $z_1$ correspond to displacements along the x, y, and z axes, subscripts $x_2$, $y_2$, and $z_2$ correspond to derivatives with respect to the x, y, and z axes, $\omega$ is an angular rate, $\hat{\omega}$ is an angular rate estimate, J is a moment of inertia, $\hat{\zeta}$ is a torque estimate, $\hat{m}_\zeta$ is a torque frequency estimate ($\hat{m}_{\zeta_x}$ is a torque frequency estimate about the x-axis, $\hat{m}_{\zeta_y}$ is a torque frequency estimate about the y-axis, $\hat{m}_{\zeta_z}$ is a torque frequency estimate about the z-axis), B is an angular rate bias, $\hat{B}$ is an angular rate bias estimate, $\hat{x}_2$ is a velocity estimate along x-axis, $\hat{y}_2$ is a velocity estimate along y-axis, $\hat{z}_2$ is a velocity estimate along z-axis, $\hat{f}$ is a force estimate, $\hat{m}_f$ is a force frequency estimate, $\hat{\phi}$ is a pitch estimate, $\hat{\theta}$ is a roll estimate, g is acceleration due to gravity, and $L_1$-$L_{29}$ are twenty-nine unknown design gains.

5. The inertial measurement unit of claim 4, wherein the twenty-nine equations utilize a full-order unknown input observer for the object in motion.

6. The inertial measurement unit of claim 1, wherein the system of motion equations utilize a reduced-order unknown input observer.

7. The inertial measurement unit of claim 1, wherein the object in motion is a golf club.

8. The inertial measurement unit of claim 7, wherein the IMU is positioned within a club head of the golf club.

9. The inertial measurement unit of claim 1, wherein the input force and the input torque are modelled as sinusoidal functions with unknown frequencies.

10. The inertial measurement unit of claim 1, wherein the system of motion equations compensate for gyroscope bias without using static leveling.

11. A golf club head comprising:
an accelerometer sensor;
a gyroscope sensor;
a processor; and
a non-transitory computer-readable medium storing computer-readable instructions that, when executed, cause the processor to:
receive sensor data from the accelerometer sensor and the gyroscope sensor responsive to a motion of the golf club head between a first time instant and a second time instant;
extract an acceleration measurement and an angular rate measurement from the sensor data;
construct a system of motion equations, utilizing an unknown input observer, which compensates for gyroscope bias resulting from physical hardware of the gyroscope, for the object in motion;
calculate an estimated output error using the received sensor data;
input the estimated output error into a system of motion equations for the golf club;
solve the system of motion equations; and
output functions describing a position of the golf club head between the first time instant and the second time instant.

12. The golf club head of claim 11, wherein the computer-readable instructions, when executed, further cause the processor to:
calculate and output a position of the golf club head between the first time instant and the second time instant using functions describing an input force, an input torque, a roll angle and a pitch angle.

13. The golf club head of claim 12, wherein the system of motion equations comprises twenty-nine coupled differential equations of the form:

$$\frac{d\hat{\omega}_x}{dt} = \frac{\hat{\zeta}_x}{J_x} - \frac{(J_z - J_y)}{J_x}\hat{\omega}_y\hat{\omega}_z + L_1\overline{e}; \quad \text{(Equation 1)}$$

$$\frac{d\hat{\omega}_y}{dt} = \frac{\hat{\zeta}_y}{J_y} - \frac{(J_x - J_z)}{J_y}\hat{\omega}_x\hat{\omega}_z + L_2\overline{e}; \quad \text{(Equation 2)}$$

$$\frac{d\hat{\omega}_z}{dt} = \frac{\hat{\zeta}_z}{J_z} - \frac{(J_y - J_x)}{J_z}\hat{\omega}_x\hat{\omega}_y + L_3\overline{e}; \quad \text{(Equation 3)}$$

$$\frac{d\hat{\zeta}_{x_1}}{dt} = \hat{\zeta}_{x_2} + L_4\overline{e}; \quad \text{(Equation 4)}$$

$$\frac{d\hat{\zeta}_{x_2}}{dt} = \hat{m}_{\zeta_x}\hat{\zeta}_{x_1} + L_5\overline{e}; \quad \text{(Equation 5)}$$

$$\frac{d\hat{m}_{\zeta_x}}{dt} = L_6\hat{\zeta}_{x_1}\overline{e}; \quad \text{(Equation 6)}$$

$$\frac{d\hat{\zeta}_{y_1}}{dt} = \hat{\zeta}_{y_2} + L_7\overline{e}; \quad \text{(Equation 7)}$$

$$\frac{d\hat{\zeta}_{y_2}}{dt} = \hat{m}_{\zeta_y}\hat{\zeta}_{y_1} + L_8\overline{e}; \quad \text{(Equation 8)}$$

$$\frac{d\hat{m}_{\zeta_y}}{dt} = L_9\hat{\zeta}_{y_1}\overline{e}; \quad \text{(Equation 9)}$$

$$\frac{d\hat{\zeta}_{z_1}}{dt} = \hat{\zeta}_{z_2} + L_{10}\overline{e}; \quad \text{(Equation 10)}$$

-continued $$\frac{d\hat{\zeta}_{z_2}}{dt} = \hat{m}_{\zeta_z}\hat{\zeta}_{z_1} + L_{11}\overline{e};$$ (Equation 11)

$$\frac{d\hat{m}_{\zeta_z}}{dt} = L_{12}\hat{\zeta}_{z_1}\overline{e};$$ (Equation 12)

$$\frac{d\hat{B}_x}{dt} = L_{13}\overline{e};$$ (Equation 13)

$$\frac{d\hat{B}_y}{dt} = L_{14}\overline{e};$$ (Equation 14)

$$\frac{d\hat{B}_z}{dt} = L_{15}\overline{e};$$ (Equation 15)

$$\frac{d\hat{x}_2}{dt} = \hat{\omega}_z\hat{y}_2 - \hat{\omega}_y\hat{z}_2 - \sin(\hat{\theta})g + \frac{\hat{f}_{x_1}}{(\text{mass})} + L_{16}\overline{e};$$ (Equation 16)

$$\frac{d\hat{y}_2}{dt} = -\hat{\omega}_z\hat{x}_2 + \hat{\omega}_x\hat{z}_2 + \sin(\hat{\phi})\cos(\hat{\theta})g + \frac{\hat{f}_{y_1}}{(\text{mass})} + L_{17}\overline{e};$$ (Equation 17)

$$\frac{d\hat{z}_2}{dt} = \hat{\omega}_y\hat{x}_2 - \hat{\omega}_x\hat{y}_2 + \cos(\hat{\theta})\cos(\hat{\phi})g + \left(\frac{\hat{f}_{z_1}}{(\text{mass})} - g\right) + L_{18}\overline{e};$$ (Equation 18)

$$\frac{d\hat{f}_{x_1}}{dt} = \hat{f}_{x_2} + L_{19}\overline{e};$$ (Equation 19)

$$\frac{d\hat{f}_{x_2}}{dt} = -\hat{m}_{f_x}\hat{f}_{x_1} + L_{20}\overline{e};$$ (Equation 20)

$$\frac{d\hat{m}_{f_x}}{dt} = L_{21}\hat{f}_{x_1}\overline{e};$$ (Equation 21)

$$\frac{d\hat{f}_{y_1}}{dt} = \hat{f}_{y_2} + L_{22}\overline{e};$$ (Equation 22)

$$\frac{d\hat{f}_{y_2}}{dt} = -\hat{m}_{f_y}\hat{f}_{y_1} + L_{23}\overline{e};$$ (Equation 23)

$$\frac{d\hat{m}_{f_y}}{dt} = L_{24}\hat{f}_{y_1}\overline{e};$$ (Equation 24)

$$\frac{d\hat{f}_{z_1}}{dt} = \hat{f}_{z_2} + L_{25}\overline{e};$$ (Equation 25)

$$\frac{d\hat{f}_{z_2}}{dt} = -\hat{m}_{f_z}\hat{f}_{z_1} + L_{26}\overline{e};$$ (Equation 26)

$$\frac{d\hat{m}_{f_z}}{dt} = L_{27}\hat{f}_{z_1}\overline{e};$$ (Equation 27)

$$\frac{d\hat{\phi}}{dt} = \hat{\omega}_x + \hat{\omega}_y\sin(\hat{\phi})\tan(\hat{\theta}) + \hat{\omega}_z\cos(\hat{\phi})\tan(\hat{\theta}) + L_{28}\overline{e};$$ (Equation 28)

and $$\frac{d\hat{\theta}}{dt} = \hat{\omega}_y\cos(\hat{\phi}) + \hat{\omega}_z\sin(\hat{\phi}) + L_{29}\overline{e},$$ (Equation 29)

wherein subscripts x, y, and z correspond to the three mutually-perpendicular axes, subscripts $x_1$, $y_1$, and $z_1$ correspond to displacements along the x, y, and z axes, subscripts $x_2$, $y_2$, and $z_2$ correspond to derivatives with respect to the x, y, and z axes, ω is an angular rate, $\hat{\omega}$ is an angular rate estimate, J is a moment of inertia, $\hat{\zeta}$ is a torque estimate, $\hat{m}_\zeta$ is a torque frequency estimate ($\hat{m}_{\zeta_x}$ is a torque frequency estimate about the x-axis, $\hat{m}_{\zeta_y}$ is a torque frequency estimate about the y-axis, $\hat{m}_{\zeta_z}$ is a torque frequency estimate about the z-axis), B is an angular rate bias, $\hat{B}$ is an angular rate bias estimate, $\hat{x}_2$ is a velocity estimate along x-axis, $\hat{y}_2$ is a velocity estimate along y-axis, $\hat{z}_2$ is a velocity estimate along z-axis, $\hat{f}$ is a force estimate, $\hat{m}_f$ is a force frequency estimate, $\hat{\phi}$ is a pitch estimate, $\hat{\theta}$ is a roll estimate, g is acceleration due to gravity, and $L_1$-$L_{29}$ are twenty-nine unknown design gains.

14. The golf club head of claim 13, wherein the twenty-nine equations utilize a full-order unknown input observer.

15. The golf club head of claim 11, wherein the accelerometer sensor measures linear acceleration along three mutually-perpendicular axes and the gyroscope sensor measures angular velocities about the three mutually-perpendicular axes.

16. The golf club head of claim 11, wherein the estimated output error ($\overline{e}$) is modelled as a 6×1 vector of the form:

$$\overline{e}(1) = (\omega_x + B_x) - (\hat{\omega}_x + \hat{B}_x);$$

$$\overline{e}(2) = (\omega_y + B_y) - (\hat{\omega}_y + \hat{B}_y);$$

$$\overline{e}(3) = (\omega_z + B_z) - (\hat{\omega}_z + \hat{B}_z);$$

$$\overline{e}(4) = a_x - \hat{a}_x;$$

$$\overline{e}(5) = a_y - \hat{a}_y; \text{ and}$$

$$\overline{e}(6) = a_z - \hat{a}_z,$$

wherein $\omega_x$, $\omega_y$, and $\omega_z$ are measured angular rates along an x-axis, y-axis, and z-axis, respectively, $\hat{\omega}_x$, $\hat{\omega}_y$, and $\hat{\omega}_z$ are angular rate estimates along the x-axis, y-axis, and z-axis, respectively; $a_x$, $a_y$, and $a_z$ are measured linear accelerations along the x-axis, y-axis, and z-axis, respectively; $\hat{a}_x$, $\hat{a}_y$, and $\hat{a}_z$ are estimated linear accelerations along the x-axis, y-axis, and z-axis, respectively, $B_x$, $B_y$, and $B_z$ are measured angular rates biases along the x-axis, y-axis, and z-axis, respectively, and $\hat{B}_x$, $\hat{B}_y$, and $\hat{B}_z$ are angular rate bias estimates along the x-axis, y-axis, and z-axis, respectively.

17. The golf club head of claim 11, wherein the system of motion equations utilizes a reduced-order unknown input observer.

18. The golf club head of claim 11, further comprising a transceiver, wherein the computer-readable instructions, when executed, further cause the processor to:
transmit the output functions, using the transceiver, to a remote computing device.

19. The golf club head of claim 11, wherein the accelerometer, the gyroscope, the processor and the non-transitory computer readable medium are integrated into an inertial measurement unit (IMU).

20. The golf club head of claim 19, wherein the IMU is configured to be removably positioned within the golf club head.

21. A method comprising:
receiving, by a computing device, sensor data from an inertial measurement unit (IMU) coupled to an object in motion between a first time instant and a second time instant;
constructing, by the computing device, a system of motion equations utilizing an unknown input observer that compensates for gyroscope bias resulting from physical hardware of the gyroscope, for the object in motion;
calculating, by the computing device, an estimated output error using the received sensor data;
inputting, by the computing device, the estimated output error into a system of motion equations for the object;
solving, by the computing device, the system of motion equations; and outputting, by the computing device, functions describing a position of the object in motion between the first time instant and the second time instant.

22. The method of claim 21, wherein the estimated output error ($\bar{e}$) is modelled as a 6×1 vector of the form:

$\bar{e}(1) = (\omega_x + B_x) - (\hat{\omega}_x + \hat{B}_x);$ $\bar{e}(2) = (\omega_y + B_y) - (\hat{\omega}_y + \hat{B}_y);$ $\bar{e}(3) = (\omega_z + B_z) - (\hat{\omega}_z + \hat{B}_z);$ $\bar{e}(4) = a_x - \hat{a}_x;$ $\bar{e}(5) = a_y - \hat{a}_y;$ and $\bar{e}(6) = a_z - \hat{a}_z,$ wherein $\omega_x$, $\omega_y$, and $\omega_z$ are measured angular rates along an x-axis, y-axis, and z-axis, respectively, $\hat{\omega}_x$, $\hat{\omega}_y$, and $\hat{\omega}_z$ are angular rate estimates along the x-axis, y-axis, and z-axis, respectively; $a_x$, $a_y$, and $a_z$ are measured linear accelerations along the x-axis, y-axis, and z-axis, respectively; $\hat{a}_x$, $\hat{a}_y$, and $\hat{a}_z$ are estimated linear accelerations along the x-axis, y-axis, and z-axis, respectively, $B_x$, $B_y$, and $B_z$ are measured angular rates biases along the x-axis, y-axis, and z-axis, respectively, and $\hat{B}_x$, $\hat{B}_y$, and $\hat{B}_z$ are angular rate bias estimates along the x-axis, y-axis, and z-axis, respectively.

23. The method of claim 21, wherein the system of motion equations for the object comprises twenty-nine coupled differential equations of the form:

$$\frac{d\hat{\omega}_x}{dt} = \frac{\hat{\zeta}_x}{J_x} - \frac{(J_z - J_y)}{J_x}\hat{\omega}_y\hat{\omega}_z + L_1\bar{e}; \quad \text{(Equation 1)}$$

$$\frac{d\hat{\omega}_y}{dt} = \frac{\hat{\zeta}_y}{J_y} - \frac{(J_x - J_z)}{J_y}\hat{\omega}_x\hat{\omega}_z + L_2\bar{e}; \quad \text{(Equation 2)}$$

$$\frac{d\hat{\omega}_z}{dt} = \frac{\hat{\zeta}_z}{J_z} - \frac{(J_y - J_x)}{J_z}\hat{\omega}_x\hat{\omega}_y + L_3\bar{e}; \quad \text{(Equation 3)}$$

$$\frac{d\hat{\zeta}_{x_1}}{dt} = \hat{\zeta}_{x_2} + L_4\bar{e}; \quad \text{(Equation 4)}$$

$$\frac{d\hat{\zeta}_{x_2}}{dt} = \hat{m}_{\zeta_x}\hat{\zeta}_{x_1} + L_5\bar{e}; \quad \text{(Equation 5)}$$

$$\frac{d\hat{m}_{\zeta_x}}{dt} = L_6\hat{\zeta}_{x_1}\bar{e}; \quad \text{(Equation 6)}$$

$$\frac{d\hat{\zeta}_{y_1}}{dt} = \hat{\zeta}_{y_2} + L_7\bar{e}; \quad \text{(Equation 7)}$$

$$\frac{d\hat{\zeta}_{y_2}}{dt} = \hat{m}_{\zeta_y}\hat{\zeta}_{y_1} + L_8\bar{e}; \quad \text{(Equation 8)}$$

$$\frac{d\hat{m}_{\zeta_y}}{dt} = L_9\hat{\zeta}_{y_1}\bar{e}; \quad \text{(Equation 9)}$$

$$\frac{d\hat{\zeta}_{z_1}}{dt} = \hat{\zeta}_{z_2} + L_{10}\bar{e}; \quad \text{(Equation 10)}$$

$$\frac{d\hat{\zeta}_{z_2}}{dt} = \hat{m}_{\zeta_z}\hat{\zeta}_{z_1} + L_{11}\bar{e}; \quad \text{(Equation 11)}$$

$$\frac{d\hat{m}_{\zeta_z}}{dt} = L_{12}\hat{\zeta}_{z_1}\bar{e}; \quad \text{(Equation 12)}$$

-continued $$\frac{d\hat{B}_x}{dt} = L_{13}\bar{e}; \quad \text{(Equation 13)}$$

$$\frac{d\hat{B}_y}{dt} = L_{14}\bar{e}; \quad \text{(Equation 14)}$$

$$\frac{d\hat{B}_z}{dt} = L_{15}\bar{e}; \quad \text{(Equation 15)}$$

$$\frac{d\hat{x}_2}{dt} = \hat{\omega}_z\hat{y}_2 - \hat{\omega}_y\hat{z}_2 - \sin(\hat{\theta})g + \frac{\hat{f}_{x_1}}{(\text{mass})} + L_{16}\bar{e}; \quad \text{(Equation 16)}$$

$$\frac{d\hat{y}_2}{dt} = -\hat{\omega}_z\hat{x}_2 + \hat{\omega}_x\hat{z}_2 + \sin(\hat{\phi})\cos(\hat{\theta})g + \frac{\hat{f}_{y_1}}{(\text{mass})} + L_{17}\bar{e}; \quad \text{(Equation 17)}$$

$$\frac{d\hat{z}_2}{dt} = \hat{\omega}_y\hat{x}_2 - \hat{\omega}_x\hat{y}_2 + \cos(\hat{\theta})\cos(\hat{\phi})g + \left(\frac{\hat{f}_{z_1}}{(\text{mass})} - g\right) + L_{18}\bar{e}; \quad \text{(Equation 18)}$$

$$\frac{d\hat{f}_{x_1}}{dt} = \hat{f}_{x_2} + L_{19}\bar{e}; \quad \text{(Equation 19)}$$

$$\frac{d\hat{f}_{x_2}}{dt} = -\hat{m}_{f_y}\hat{f}_{x_1} + L_{20}\bar{e}; \quad \text{(Equation 20)}$$

$$\frac{d\hat{m}_{f_x}}{dt} = L_{21}\hat{f}_{x_1}\bar{e}; \quad \text{(Equation 21)}$$

$$\frac{d\hat{f}_{y_1}}{dt} = \hat{f}_{y_2} + L_{22}\bar{e}; \quad \text{(Equation 22)}$$

$$\frac{d\hat{f}_{y_2}}{dt} = -\hat{m}_{f_y}\hat{f}_{y_1} + L_{23}\bar{e}; \quad \text{(Equation 23)}$$

$$\frac{d\hat{m}_{f_y}}{dt} = L_{24}\hat{f}_{y_1}\bar{e}; \quad \text{(Equation 24)}$$

$$\frac{d\hat{f}_{z_1}}{dt} = \hat{f}_{z_2} + L_{25}\bar{e}; \quad \text{(Equation 25)}$$

$$\frac{d\hat{f}_{z_2}}{dt} = -\hat{m}_{f_z}\hat{f}_{z_1} + L_{26}\bar{e}; \quad \text{(Equation 26)}$$

$$\frac{d\hat{m}_{f_z}}{dt} = L_{27}\hat{f}_{z_1}\bar{e}; \quad \text{(Equation 27)}$$

$$\frac{d\hat{\phi}}{dt} = \hat{\omega}_x + \hat{\omega}_y\sin(\hat{\phi})\tan(\hat{\theta}) + \hat{\omega}_z\cos(\hat{\phi})\tan(\hat{\theta}) + L_{28}\bar{e}; \quad \text{(Equation 28)}$$

and $$\frac{d\hat{\theta}}{dt} = \hat{\omega}_y\cos(\hat{\phi}) + \hat{\omega}_z\sin(\hat{\phi}) + L_{29}\bar{e}, \quad \text{(Equation 29)}$$

wherein subscripts x, y, and z correspond to the three mutually-perpendicular axes, subscripts $x_1$, $y_1$, and $z_1$ correspond to displacements along the x, y, and z axes, subscripts $x_2$, $y_2$, and $z_2$ correspond to derivatives with respect to the x, y, and z axes, $\omega$ is an angular rate, $\hat{\omega}$ is an angular rate estimate, J is a moment of inertia, $\hat{\zeta}$ is a torque estimate, $\hat{m}_\zeta$ is a torque frequency estimate ($\hat{m}_{\zeta_x}$ is a torque frequency estimate about the x-axis, $\hat{m}_{\zeta_y}$ is a torque frequency estimate about the y-axis, $\hat{m}_{\zeta_z}$ is a torque frequency estimate about the z-axis), B is an angular rate bias, $\hat{B}$ is an angular rate bias estimate, $\hat{x}_z$ is a velocity estimate along x-axis, $\hat{y}_2$ is a velocity estimate along y-axis, $\hat{z}_2$ is a velocity estimate along z-axis, $\hat{f}$ is a force estimate, $\hat{m}_f$ is a force frequency estimate, $\hat{\phi}$ is a pitch estimate, $\hat{\theta}$ is a roll estimate, g is acceleration due to gravity, and $L_1$-$L_{29}$ are twenty-nine unknown design gains.

* * * * *